United States Patent [19]
Alila et al.

[11] Patent Number: 5,889,144
[45] Date of Patent: Mar. 30, 1999

[54] FUSED SOMATOTROPIN EPITOPIC PEPTIDES THAT POTENTIATE GROWTH HORMONE ACTIVITY

[75] Inventors: Hector Wasunna Alila, Malvern; Michael Thomas Clark, Downington; Elaine Verne Jones, Wynnewood; Timothy Joe Miller, Malvern; Shawn Patrick O'Brien, Hatboro; Ganesh Madhusudan Sathe, King of Prussia, all of Pa.

[73] Assignee: Pfizer Inc., New York, N.Y.

[21] Appl. No.: 846,913

[22] Filed: Apr. 30, 1997

Related U.S. Application Data

[62] Division of Ser. No. 388,267, Jan. 27, 1995, Pat. No. 5,686,268, which is a continuation of Ser. No. 901,704, Jun. 19, 1992, abandoned.

[51] Int. Cl.$^6$ .......................... C07K 14/00; C07K 14/61; C12N 15/18
[52] U.S. Cl. .......................... 530/300; 530/324; 530/350; 530/399; 435/69.7; 536/23.4; 930/120
[58] Field of Search ...................... 530/300, 323, 530/324, 345, 350, 387.1, 387.9, 399; 435/69.7; 536/23.4; 930/120

[56] References Cited

U.S. PATENT DOCUMENTS

| | | | |
|---|---|---|---|
| 4,425,437 | 1/1984 | Riggs | 435/317 |
| 4,578,355 | 3/1986 | Rosenberg | 435/317 |
| 4,803,072 | 2/1989 | Dalton et al. | 424/85.5 |
| 5,210,180 | 5/1993 | Wang et al. | 530/328 |
| 5,338,836 | 8/1994 | Wang et al. | 530/399 |
| 5,506,107 | 4/1996 | Cunningham et al. | 435/7.21 |
| 5,547,669 | 8/1996 | Rogers et al. | 424/185.1 |

OTHER PUBLICATIONS

Cunningham and Wells, 1989, High-resolution epitope mapping of hGH-receptor interactions by alanine-scanning mutagenesis, Science 244:1081–1085.

Germino and Bastia, 1984, Rapid purification of a clone gene product by genetic fusion and site-specific proteolysis, Proc. Natl. Acad. Sci. USA, 81: 4692–4696.

Shen, 1984, Multiple joined genes prevent product degradation in *Escherichia coli*, Proc. Natl. Acad. Sci. USA, 81: 4627–4631.

Aston et al., 1987, Enhancement of bovine growth hormone activity in vivo by monoclonal antibodies, Mol. Immun., 24:143–150.

Li et al., 1974, Human pituitary growth hormone: isolation and properties of two biologically active fragments from plasmin digests, Proc. Natl. Acad. Sci. USA 71:1197–1201.

Aston et al., 1983, Antigenic, receptor-binding and mitogenic activity of proteolytic fragments of human growth hormone, EMBO, 2:493–497.

Seeburg et al, 1983, Efficient bacterial expression of bovine and porcine growth hormones, DNA 2:37–45.

Young et al., 1983, Efficient bacterial expression of influenza virus NS1 nonstructural proteins in E. coli, Proc. Natl. Acad. Sci. USA 80:6105–6109.

Aston et al., 1991, Antigenic structure of a bovine growth hormone: location of a growth enhancing region, Mol. Immunol. 28:41–50.

*Primary Examiner*—John Ulm
*Assistant Examiner*—Christine Saoud
*Attorney, Agent, or Firm*—Peter C. Richardson; Paul H. Ginsburg; Alan L. Koller

[57] ABSTRACT

This invention relates to composite somatotropin peptides comprising somatotropin epitopic amino acid sequences, and fusion proteins thereof, useful in potentiating growth hormone activity. Also disclosed are vectors and host cells useful in the recombinant production of such molecules. Vaccines containing the composite somatotropin peptides and fusion proteins of the present invention, and methods of using the same, are disclosed.

15 Claims, 8 Drawing Sheets

```
                EcoRI
                  1
TTTACGAATTCCCTGGTTTTTGGCACATCCGACACAGAGCATATATTCCCGAAGGCCAGCGT
AAATGCTTAAGGGACCAAAAACCGTGTAGGCTGTGTCTCGTATATAAGGGCTTCCGGTCGCA
                                                      2
PheThrAsnSerLeuValPheGlyThrSerAspArgAlaTyrIleProGluGlyGlnArg
                                 3
TATTCCATTCAGAATGCACAGGCAGCATTTGTTTCCAGGCACTGATGAGAACTGGAA
ATAAGGTAAGTCTTACGTGTCCGTCGTAAACAAAGGTCCGTGACTACTCTCTTGACCTT
                4
TyrSerIleGlnAsnAlaGlnAlaAlaPheCysPheGlnAlaLeuMetArgGluLeuGlu
          BamHI                                NdeI
                  5
GACGGATCCCCCAGAGCAGGCCAGATTCTGAAACACATATGACAAATTTGACACAAAC
CTGCCTAGGGGGTCTCGTCCGGTCCTAAGACTTTGTGTCTGTATACTGTTTAAACTGTGTTTG
                                    6
AspGlySerProArgAlaGlyGlnIleLeuLysGlnThrTyrAspLysPheAspThrAsn
         7
CTGAGATCCTGATAAC
GACTCTAGGACTATTGAGCT    XhoI
         8

FIG.1A
```

FUSED SOMATOTROPIN EPITOPIC PEPTIDES THAT POTENTIATE GROWTH HORMONE ACTIVITY

This is a division of application Ser. No. 08/388,267, filed on Jan. 27, 1995, now U.S. Pat. No. 5,686,268, which is a continuation of application Ser. No. 07/901,704, filed Jun. 19, 1992, now abandoned.

FIELD OF THE INVENTION

This invention relates to synthesis, cloning, and expression of fused proteins. More specifically, this invention relates to peptides comprising epitopes of porcine somatotropins (pST) fused to a non-related peptide and the use of the resulting fused protein to potentiate pST activity following immunization.

BACKGROUND OF THE INVENTION

In what may be considered to be, at first blush, counterintuitive, it has been appreciated for some time that antisera raised against hormone antigens are not necessarily inhibiting but can, in fact, potentiate hormone activity in vitro and in vivo (Thompson, K. W., *Proc. Soc. Exp. Biol. Med.* 35:640–44 (1937) and Rowlands, I. W., *J. Endocrinol.* 1:177–183 (1939). Antibody-mediated enhancement of hormone activity has been reviewed by Aston et al., (*Molecular Immunol.* 26(5):435–446 (1989)), the contents of which are incorporated herein by reference to more fully describe the background of this invention. Of relevance to this invention are the observations regarding the beneficial effect of antibodies raised to growth hormones, more particularly, porcine growth hormone.

The amino acid sequence has been determined for growth hormone from numbers of species including human growth hormone (hGH), porcine (pGH), bovine (bGH), horse (hoGH), rat (rGH), monkey (mGH), avian (aGH), fish (fGH), canine (cGH), and ovine (oGH) (See for example: Seeburg, P. H. et. al., *DNA* 2(1) :37–45 (1983); Abdel-Mequid, S. S. et. al., *Proc. Nat'l. Acad. Sci.* (USA) 84:6434–37 (1987)). Growth hormone, also referred to in the literature as somatotropin (ST), is a 22,000 dalton protein secreted by the anterior pituitary gland in mammals. In its native form the molecule contains 190 amino acids. Because the native form results from the cleavage of a 26 amino acid signal sequence from a larger precursor molecule, there can be some $NH_2$-terminal length polymorphism due to inefficient post-translational processing. Accordingly, both 190 amino acid $NH_2$-terminal phenylalanine and 191 amino acid $NH_2$-terminal alanine forms are known (Mills, J. B. et. al., *J. Biol. Chem.* 245:3407–15 (1970)). Although some variation occurs, the above-mentioned somatotropins share a good deal of structural and functional homology such that epitope regions identified in one species are good predictors for analogous regions in another species.

The nucleotide and amino acid sequences of pST are reported in Seeburg et. al. (supra) including 20 amino acids of the leader peptide. The nucleotide and amino acid sequences represented by Sequences I.D. Nos. 1 and 2 respectively.

Aston et. al., reported the potentiation of the somotogenic and lactogenic activity of hGH (*J. Endocrinol.* 110:381–388 (1986) and bGH (*Mol. Immunol.* 24(2):143–150 (1987)) by monoclonal antibodies when given in combination with these hormones.

EP Application 0284406, published Sep. 28, 1988, relates to certain growth hormone fragments spanning positions 35 to 53 and antigenic formulations thereof useful in potentiating the effects of growth hormone.

Similarly, PCT Application W089/001666, published Jan. 12, 1989, relates to antibodies raised to antigenic peptides spanning the region 112–159 of native growth hormone and portions thereof coupled to a carrier. The antibodies were shown to potentiate growth hormone effects. Porcine growth hormone regions 134–154 and 120–140 and fragments thereof were specifically identified.

EP Application 0303488, published Feb. 15, 1989, specifically identifies the following regions 1 to 18, 55–72, 97–110, 119–131, 122–138, 123–137, 130–143, and 133–146 as useful as components of antigenic formulations. The antibodies generated to the foregoing peptides have growth hormone enhancing effects.

EP Application 0492788, published Jun. 5, 1991, identifies additional pST regions said to be useful for generating antibodies in pigs and rabbits. Regions specifically mentioned include 98–110, 110–118, and 155–163.

More recently, the epitopes on bGH have been identified as being included within regions 120–140 and 134–154. Aston et. al., *Mol. Immunol.* 28(1/2):41–50 (1991).

The individual peptide epitopes, such as those described above, are known to function individually. Furthermore, these fragments were chemically synthesized and as such were not amendable to scale-up for commercial vaccine production. This invention employs a recombinant DNA approach in which at least two distinct epitopes are biosynthesized as a composite peptide molecule. This molecule can be then coupled chemically to a carrier to enhance immunogencity, or more preferrably, the DNA encoding the composite molecule can be operatively linked, in frame, with the DNA encoding a non-related peptide; the entire construction upon expression results in a fusion protein which then may be used directly or be optionally chemically coupled to a carrier.

BRIEF DESCRIPTION OF THE INVENTION

This invention relates to composite peptides comprising at least two non-contiguous somatotropin epitopic amino acid sequences.

This invention also relates to fusion proteins comprised of a composite somatotropin peptide linked to a non-related protein.

This invention also relates to both composite peptides or fusion proteins optionally linked to a carrier molecule.

This invention further relates to isolated DNAs encoding the aforesaid composite peptides and fusion proteins, expression vectors comprising those DNAs and host cells transformed by the expression vectors.

This invention further relates to vaccines comprising the composite peptides or fusion proteins.

This invention also relates to the recombinant production of the composite peptides and fusion proteins.

This invention also relates to a method for potentiating the action of growth hormone in a pig comprising inducing an antibody response to the composite peptide of any of the Claims 1–17, 28, and 29 and treating said induced pig with a growth enhancing amount of pST.

Nucleotide sequence was slightly altered without changing the encoded amino acids to create unique restriction sites.

Figure 1B:
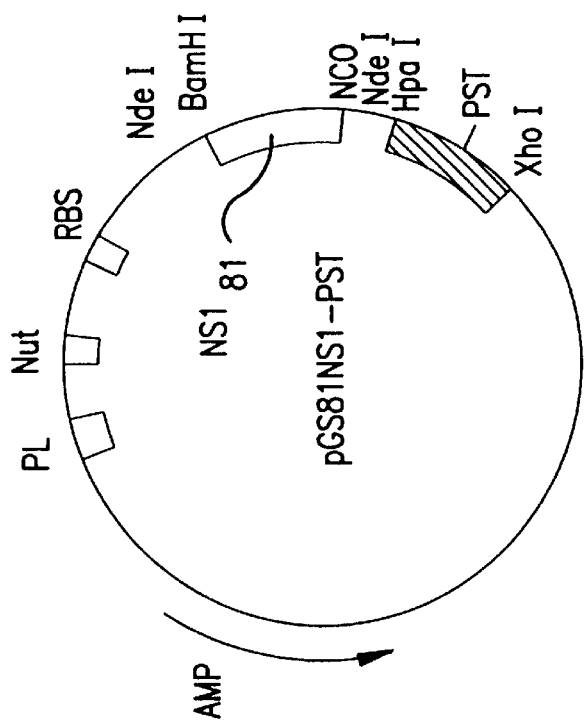
FIG. 1A illustrates the nucleotide and amino acid sequence of a synthetic pST composite gene (SEQ. ID. NOS. 8, 23, 24). Numbers denote the synthetic oligomers.

FIG. 1B illustrates the cloning of a synthetic pST composite gene in the E. coli expression vector, pMG-1. The gene was cloned downstream and in frame with the first 81 amino acids of influenza nonstructual gene, NS1. The resultant plasmid is named pGS81NSI-pST.

Figure 2:
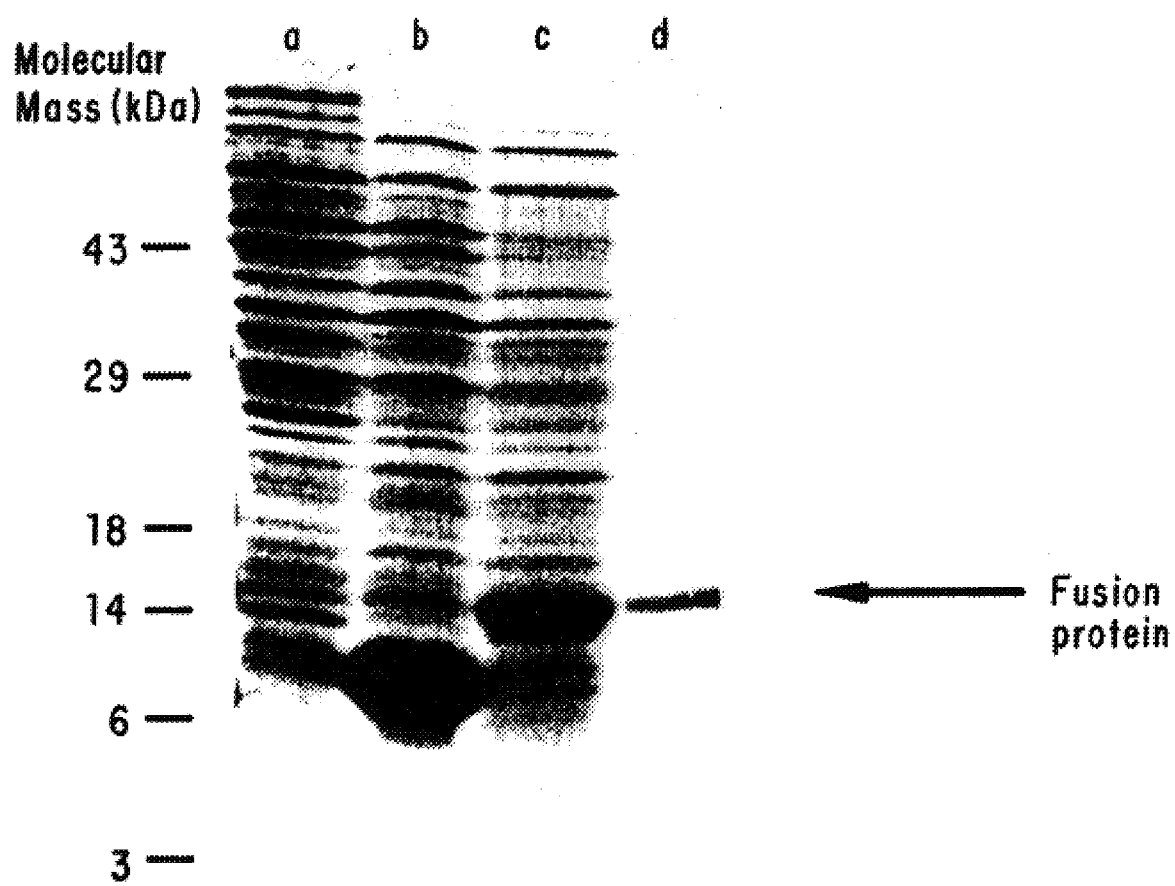

FIG. 2 illustrates the expression of NS1-pST composite fusion protein in bacteria. E. coli strain AR58 was transformed with pMG-1 and pGS81NS1-pST plasmids individually and grown to $A_{600}$ of 0.6 in L broth at 32° C. The incubation temperature was then increased to 42° C. for 3 hours to induce expression of the NS1-pST composite fusion protein. Bacteria were pelleted and lysed by addition of Laemmli sample buffer. Polyacrylamide gels were electrophoresed to analyze the lysates from the induced cultures. Duplicate gels were transferred to nitrocellulose for Western blot analysis. Coomassie blue stained gel of proteins present in induced lysates are shown.

Lane a: 0 min time point
Lane b: pMG-1,t=3h
Lane c: pGS81NS1-pST,t=3h
Lane d: gel purified NS1-PST composite fusion protein FIG. 3 illustrates Western blot analysis of NS1-pST composite fusion protein.

Figure 3A:
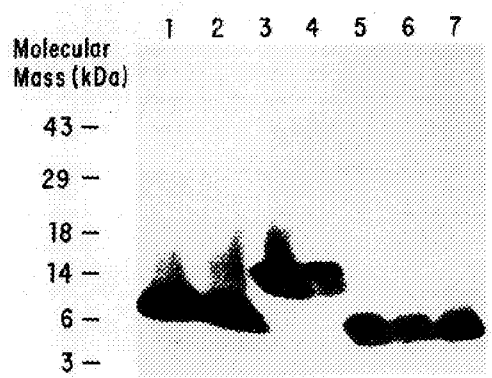

FIG. 3A illustrates a Western blot using NS1 antiserum. Lanes 1, 2, 5, 6, and 7 contain lysates of pMG-1, expressing only the 81 amino acids of influenza NS1. Lanes 3 and 4 contain lysates of PGS81NS1-PST, expressing the NS1-PST fusion protein.

Figure 3B:
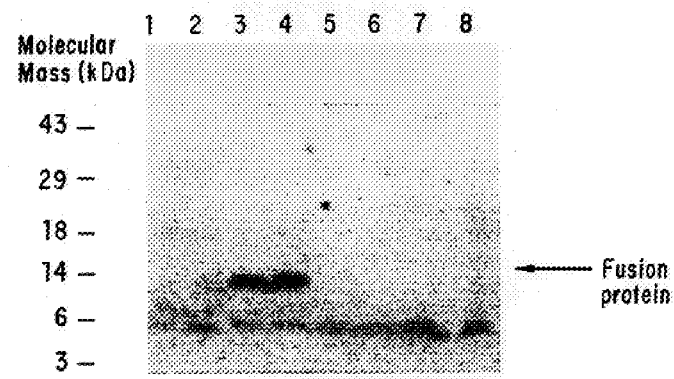

FIG. 3B illustrates a Western blot using antiserum to denatured pST. Lanes 1, 2, 5, 6, 7, and 8 contain lysates of pMG-1 expressing influenza NS1 protein alone. Lanes 3 and 4 contain lysates of pGS81NS1-pST, expressing the NS1-pST composite fusion protein.

Figure 4:
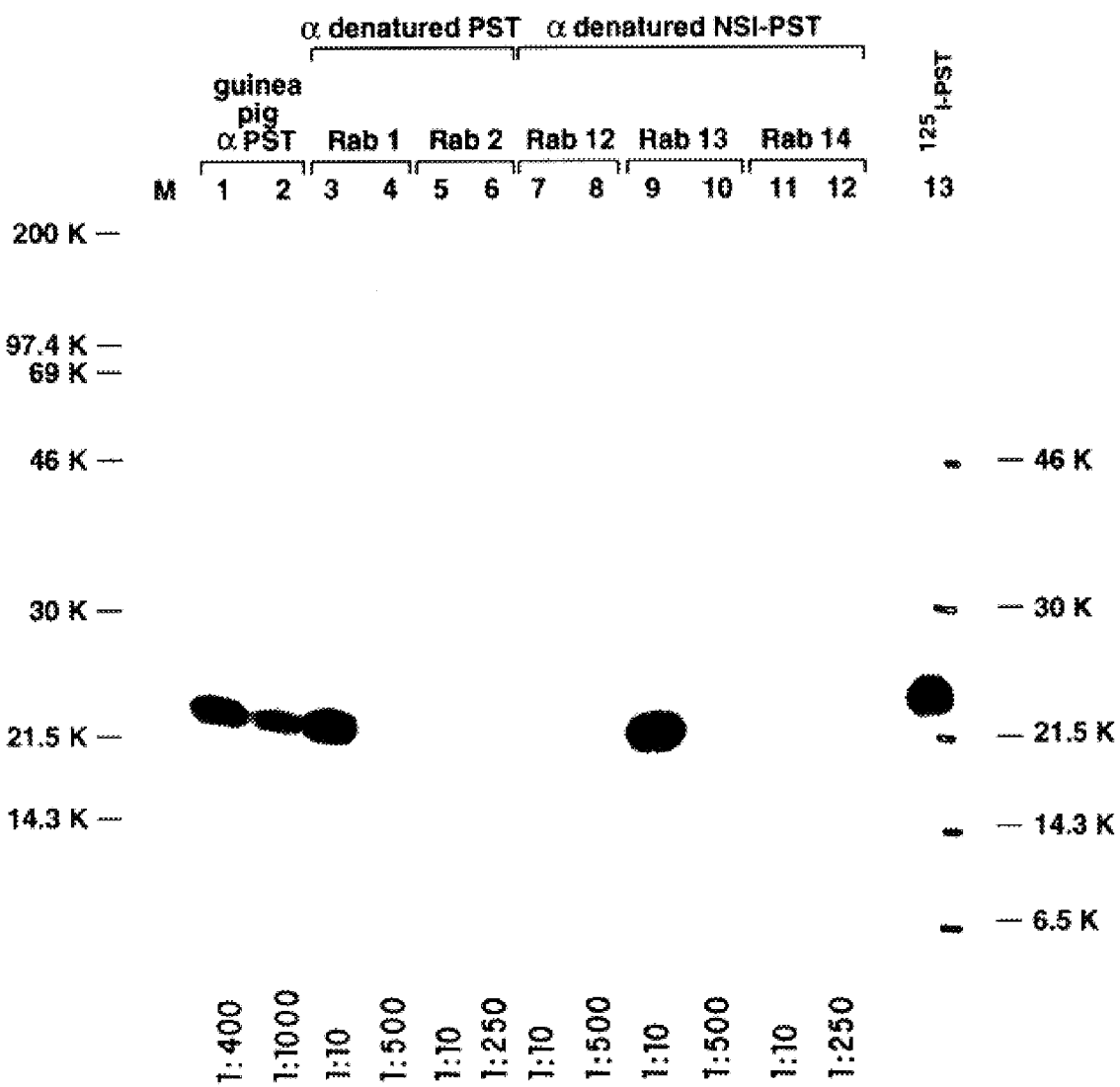

FIG. 4 illustrates the immunoprecipitation of $^{125}$I-pST with antisera from rabbits immunized with NS1-pST fusion protein. Iodinated pST was first reacted with preimmune sera from either guinea pig or rabbit for 60 min on ice. Staph A conjugated to Sepharose CL-4B beads was added for 30 min on ice. Immune complexes were pelleted by centrifugation in a microfuge for 2 min. The supernatants were removed to a fresh tube and then incubated with the indicated dilutions of guinea pig sera prepared against pST or with sera from the rabbits immunized with either pST(#1, #2) or NS1-pST(#12, #13, #14) for 60 min on ice. Staph A-coated Sepharose beads were added and after 30 min on ice, the immune complexes were collected by centrifugation. The immunoprecipitates were washed 4 times with RIPA and boiled in SDS sample buffer prior to loading on a SDS polyacrylamide gel.

Figure 5:
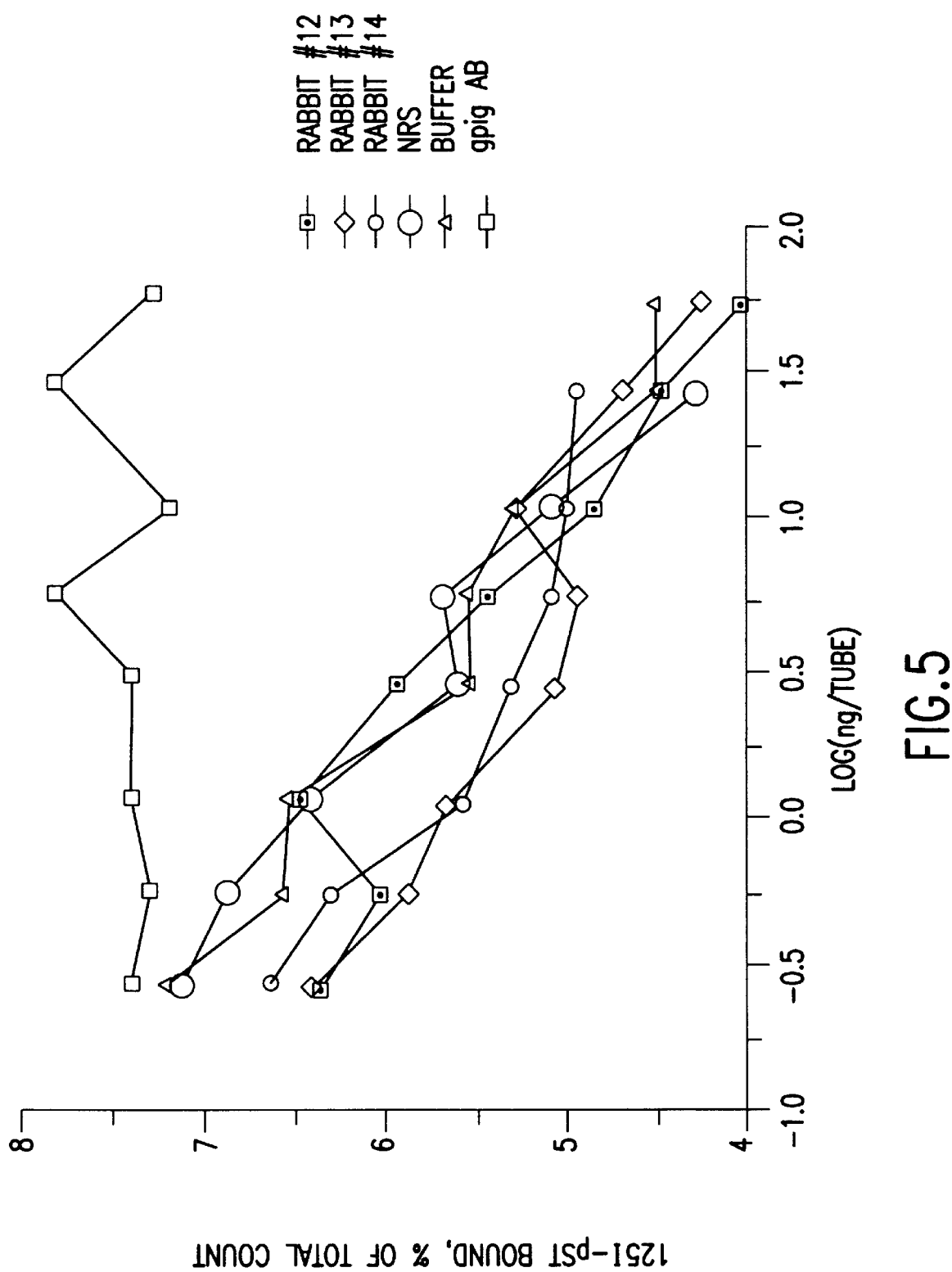

FIG. 5 illustrates the effects of rabbit antisera (1:1000) on the ability of increasing concentrations of unlabelled pST to displace $^{125}$I-pST binding to liver membranes. Controls used were normal rabbit serum (NRS), assay buffer and guinea pig antibody to native pST (1:1000).

Figure 6:
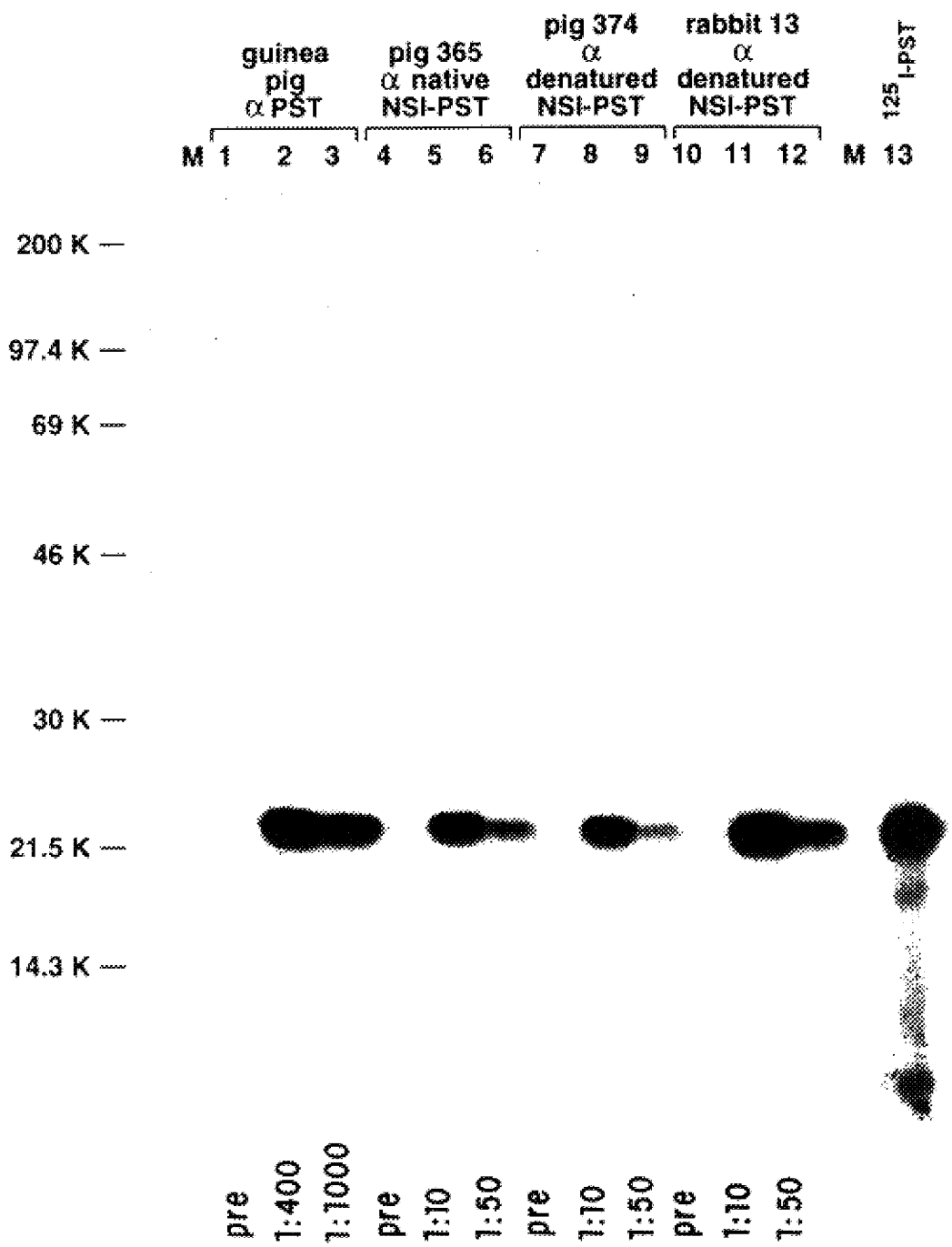

FIG. 6 illustrates the immunoprecipitation of $^{125}$I-pST with antisera from pigs immunized with NS1-pST fusion protein. Iodinated pST was first reacted with preimmune sera from either guinea pig, rabbit or pig for 60 min on ice. Staph A conjugated to Sepharose CL-4B beads was added for 30 min on ice. Immune complexes were pelleted by centrifugation in a microfuge for 2 min. Pellets from incubation of preimmune sera were boiled in SDS sample buffer in preparation for electrophoresis. The supernatants were removed to a fresh tube and then incubated with the indicated dilutions of 1) guinea pig sera prepared against pST; 2) sera from a rabbit immunized with NS1-pST (#13); or, 3) sera from pigs immunized with NS1/pST (#365) or NS1/pST treated with 0.1% SDS (#371) for 60 min on ice. Staph A-coated Sepharose beads were added and after 30 min on ice, the immune complexes were collected by centrifugation. The immunoprecipitates were washed 4 times with RIPA and boiled in SDS sample buffer prior to loading on a SDS polyacrylamide gel.

Figure 7:
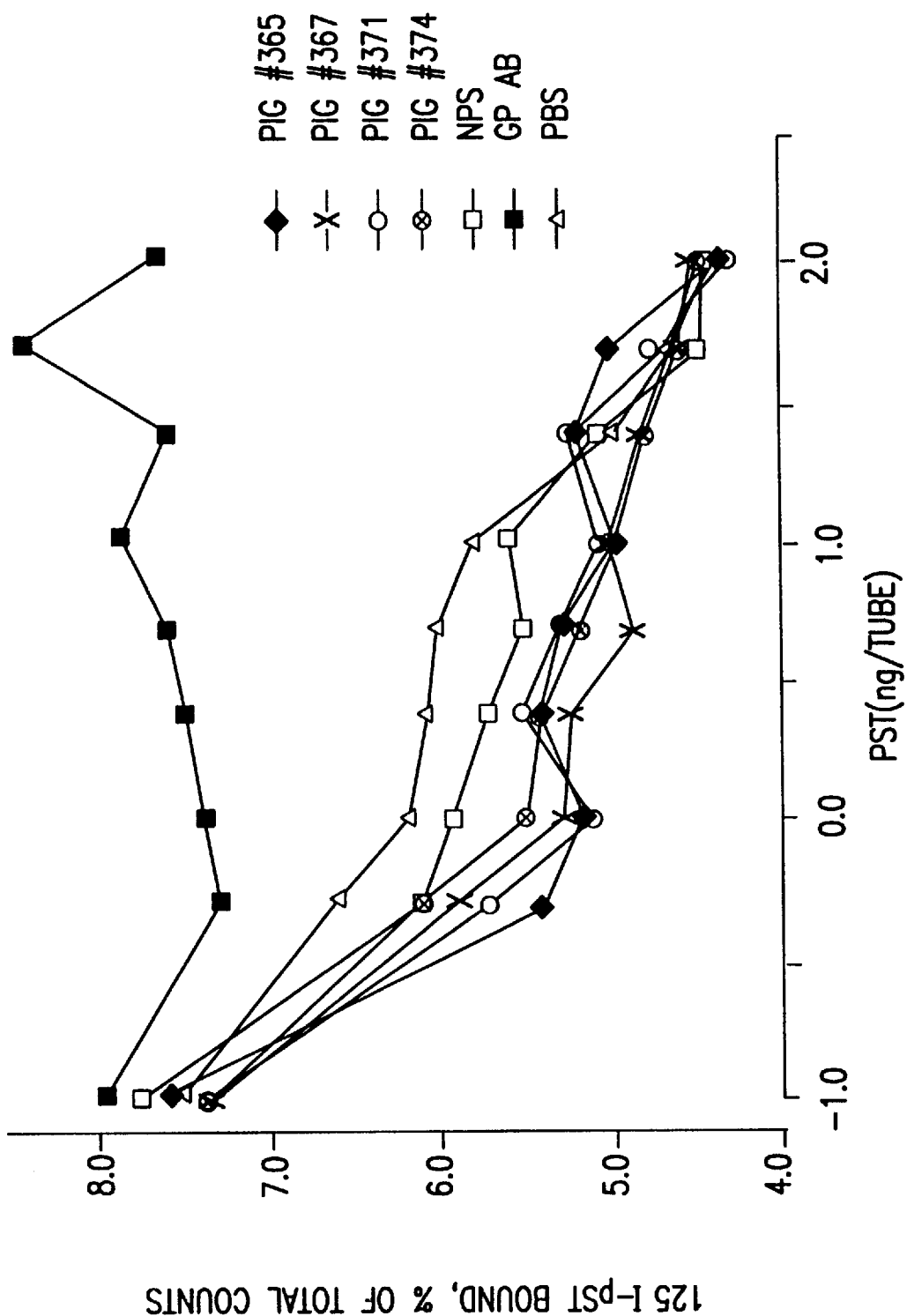

FIG. 7 illustrates the effects of sera from immunized pigs on the ability of increasing concentrations of unlabelled pST to displace $^{125}$I-pST binding to liver membranes. Pigs #365 and 367 were immunized with NS1/pST protein ("native") while pigs #371 and 374 were immunized with NS1/pST fusion protein which had been denatured with 0.1% SDS. Controls used were normal pig sera (NPS), assay buffer (PBS) and guinea pig antibody (GP AB) to pST at 1:1000 dilution.

DETAILED DESCRIPTION OF THE INVENTION

This invention describes the design, construction, and use of a recombinant composite peptide comprising selected regions of somatotropin (ST). Optionally, the composite peptide is fused to a non-related protein, such as influenza nonstructual protein (NS1), to potentiate ST activity in vivo following immunization. The fusion protein may be further chemically complexed with a carrier prior to immunization. In particular, porcine somatotropin (pST) constructions are employed in the immunization of pigs to modulate feed efficiency and growth.

Even though the relevant peptides and proteins are identified by sequence number and appear in the sequence number listing infra, these molecules are also referred by the following format which is conventional in the art to which this invention relates. Accordingly, the 190 amino acid full-length porcine somatotropin having an $NH_2$-phenylalanine residue as described in Seeburg et al. (supra) is referred as $pST_{1-190}$ or $pST_{190}$. The $NH_2$-terminal polymorphic form having 191 amino acids and a $NH_2$-terminal alanine is referred to as ala-$pST_{1-190}$, $pST_{1-191}$, or $pST_{191}$. Fragments of these molecules are referred to by their amino-terminal and carboxy-terminal residue number, i.e., 33–53 $pST_{190}$ or 96–106 $pST_{191}$.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen."

The term "epitope" refers to the site on an antigen or hapten to which a specific antibody molecule binds. The term is also used interchangeably with "antigenic determinant" or "antigenic determinant site."

"Native" proteins or polypeptides refer to proteins or polypeptides recovered from a source ocurring in nature. Thus, the term "native pST" would include $pST_{1-190}$ and $pST_{1-191}$.

"Composite peptide" is a peptide in which two or more normally non-contiguous somatotropin epitopes are synthesized as a single polypeptide without normally intervening sequences.

"Fusion protein" is a protein resulting from the expression of at least two operatively-linked heterologous coding sequences. The protein comprising NS1 peptide and composite somatotropin peptide sequences of this invention is an example of a fusion protein.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desire protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide in vivo when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience. Ausbel et al. (ed.) (1992).

The term "functionally equivalent" intends that the amino acid sequence of the subject protein is one that will elicit an immunological response, as defined above, equivalent to the specified composite pST peptide.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of a heterologous coding sequence is a construct where the coding sequence itself is not found in nature (e.g., synthetic sequences having codons different from the native gene). Allelic variation or naturally occuring mutational events do not give rise to a heterologous region of DNA, as used herein.

An epitopic amino acid sequence is "substantially free of" receptor binding domain sequences when at least about 85% of the amino acids of the total sequence are not involved with receptor binding. Preferably, at least about 90% of the total sequence in the composition, more preferably at least about 95%, or even 99% of the total.

An "immunological response" to a composition or vaccine is the development in a vertebrate of a cellular and/or antibody-mediated immune response to the composition or vaccine of interest. Usually, such a response in the case of this invention consists of the subject producing antibodies that potentiate the action of porcine somatotropin.

As mentioned above, it is an object of this invention to produce fusion proteins comprised of selected pST epitopes, in particular non-receptor binding domains, which will induce pST potentiating antibodies in pigs following immunization. The resultant antibodies would bind to pST in circulation without adversely affecting its biological activity, increasing the half-life and/or potentiating the action of the hormone by improving feed efficiency and growth. Among the novel compositions disclosed are fusion proteins of pST produced by recombinant techniques. The fusion proteins were designed to raise antibodies that would not interfere with pST binding to its receptor.

The three dimensional structure of pST (Abdel-Meguid et. al., (1987) supra) combined with biological characterization of the hormone have mapped the receptor binding domains of the hormone. It is also feasible, to produce antibodies, which have long half-lives in serum, which bind but do not interfere with the growth promoting activity of the hormone by selecting epitopes that are analogous to pST by reference to homologous regions in somatotropins of other species, e.g. hST as disclosed by devos at al. *Science* 255:306–312 (1992).

Although not wishing to be bound to any particular theory of mechanism of action, it is believed that the antibodies induced by the administration of the immunogens of this invention potentiate the action of pST by one or more of the following possibilities, inter alia, prolonging the half-life of pST in circulation, improving delivery of pST to liver cells, increasing uptake efficiency at the target cell surface, lengthening the time of interaction with the pST receptor by retarding internalization, restricting pST interaction with somatogenic receptors and/or altering pST molecular configuration to enhance its interaction with responsive cellular components.

A variety of pST sequences may be employed as epitopic sequences. As mentioned previously, it is preferred that the epitopes be substantially free of receptor binding domain sequences as that term is defined hereinabove. Stating it somewhat differently, the fact that a potential epitope sequence contains one or a few amino acids associated with a receptor binding domain is not necessarily fatal to the use of such an epitope in the practice of this invention. However, the percentage of receptor binding domain amino acids should be less than 15% of the total amino acids in the sequence, more preferable, less than 10%, and most preferably 5% or 1% or less. Useful epitope sequences that may be used to construct composite somatotropin of this invention include, but are not limited to, 33–53pST$_{190}$ (SEQ ID NO:5), 35–53pST$_{191}$ (SEQ ID NO:6), 35–43pST$_{191}$ (SEQ ID NO:7); 35–48pST$_{191}$ (SEQ ID NO:10), 96–106pST$_{190}$ (SEQ ID NO:11), 98–110pST$_{191}$ (SEQ ID NO:12), 110–118pST$_{191}$ (SEQ ID NO:13), 119–131pST$_{191}$ (SEQ ID NO:14), 120–140pST$_{191}$ (SEQ ID NO:15), 120–150pST$_{190}$ (SEQ ID NO:16), 122–138pST$_{191}$ (SEQ ID NO:17), 123–137pST$_{191}$ (SEQ ID NO:18), 130–143pST$_{191}$ (SEQ ID NO:19), 133–146pST$_{191}$ (SEQ ID NO:20), 134–154pST$_{191}$ (SEQ ID NO:21), and 155–163pST$_{191}$ (SEQ ID NO:22). Additional sequences or subfragments of the above-recited sequences may also be used. A subfragment would include any sequence of at least six amino acids contained within the defined fragment. For example, if a defined fragment contained a 10 amino acid sequence, a subfragment would be any sequence contained within the defined sequence of at least 6 amino acids, 1–6, 2–7, 3–8, 5–10, etc. See for example PCT Application W089/00166 published Jan. 12, 1989, for additional illustration of the subfragment concept. To determine if a particular sequence is useful, all that the ordinary skilled artisan needed do is to test the sequence or the antibody raised thereto in the radioreceptor assay described in Example I. A molecule that does not compete or competes poorly with pST for receptor binding is useful as an epitope component of a composite peptide.

Two or more sequences representing non-receptor binding epitopes such as those listed above are selected and synthesized as a single polypetide chain, resulting in a composite somatotropin of non-contiguous epitopes. Furthermore, with respect to the orientation of the epitopes, it is not necessary that the components retain their normal NH$_2$ to COOH-terminal relationship with each other. That is to say, if fragments 35–53pST$_{191}$ and 133–146pST$_{191}$ are selected, the NH$_2$ to COOH orientation can be (133–146)pST$_{191}$-(35–53)pST$_{191}$. In fact, one of the preferred three epitope-containing composites of this invention has the orientation NH$_2$-(96–106)pST$_{190}$-(33–53)pST$_{190}$-(120–150)pST$_{190}$-COOH (SEQ ID NO:9).

The composites themselves may be immunogenic, but it is preferred to synthesize the composite in the form of a fusion protein. A fusion protein results from the expression of a gene that has two distinct coding regions operatively linked in the same reading frame. See for example U.S. Pat. No. 4,425,437. In the case of this invention, a first coding region encoding a non-related protein such as β-galactosidase, R32, galK, or the influenza NS1 protein is operatively linked to a coding region encoding a composite somatotropin epitopic peptide. The use of a fusion protein may have one or more of the following beneficial results: 1) enhancing expression of the protein in bacteria so that large scale production of the antigen is economically feasible; 2) permiting immunological detection of the fusion protein; 3) increasing the antigencity of the epitopes; and 4) allowing the protein to assume some secondary structure so that antibody generation is enhanced and more likely to bind native hormone.

According to current immunological theories, a carrier function is also usefully employed in any immunogenic formulation in order to stimulate, or enhance stimulation of, the immune system. It is thought that carriers inter alia embody (or, together with antigen, create) a helper T-cell epitope. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, myoglobin, bacterial toxoids or toxins, and other proteins well known to those skilled in the art. Most useful are commercially available activated bovine serum albumins, such as Imject Supercarrier System (Pierce). Some of these latter compounds may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclo-hexane-1-carboxylate, the latter agent could exploit the -SH group on the C-terminal cysteine residue of the 35–53pST$_{191}$ region.

Although the composite peptide can be made synthetically, for example by employing a Biosearch 9600 (Milligen Biosearch, Burlington, Mass.) solid phase peptide synthesizer and then chemically cross-linked to the appropriate carrier, it is preferred to employ recombinant DNA techniques for the synthesis of the composite and most preferable to use recombinant techniques to synthesize the composite and nonrelated sequence as a single fusion protein which then can be complexed with a carrier.

Once the desired epitopes have been identified, nucleic acid sequences encoding the epitopes are synthesized by conventional techniques such as those described in the Example herein. The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transorm include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, , YCp19 (Saccharomycs) and bovine papilloma virus (mammalian cells). See, generally, "DNA Cloning": Vols. I & II, Glover et. al. ed. IRL Press Oxford (1985) (1987) and; T. Maniatis et. al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the antigens of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform *E coli* and pooling and screening individual colonies using polyclonal serum or monoclonal antibodies to the desired antigen.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not preferred, particularly when complex composite proteins and fusion proteins capable of raising an immunological response are the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et. al., "Hybridoma Techniques" (1980); Hammerling et. al., "Monoclonal Antibodies and T-cell Hybridomas" (1981); Kennett et. al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the invididual antigens which they are directed against. Alternatively, genes encoding the monoclonals of interest may be isolated from the hybridomas by PCR techniques known in the art and cloned and expressed in the appropriate vectors. The recombinantly produced monoclonals can be used as a source of antibodies for passive immunization to potentiate the growth hormone response as described herein. The antibodies of this invention, whether polyclonal or monoclonal have additional utility in that they may be employed reagents in immunoassays, RIA, ELISA, and the like.

Animals, such as pigs, can be immunized with the composite peptide or fusion proteins of the present invention by administration of the composite peptide or fusion protein of interest. The immunogen will include the amino acid sequence of at least two epitopes which interact with the immune system to immunize the animal to those and structually similar epitopes.

Of course, as specifically exemplified, it is preferred to recombinantly express the genetic information encoding the composite protein operably linked with the genetic information encoding a non-related protein so as to provide a fusion protein having both elements.

The novel composite or fusion proteins of this invention can also be administered via a carrier virus which expresses the same. Carrier viruses which will find use with this invention include but are not limited to the vaccinia and other pox viruses, adenovirus, baculovirus, and herpes virus. By way of example, vaccinia virus recombinants expressing the novel proteins can be constructed as follows: The DNA encoding the particular protein is first inserted into an apprpriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK recombinant can be selected by culturing the cells in the presence of 5-bromodeoxyuridine and picking viral plaques resistant thereto.

It is also possible to immunize a subject with the composite peptide or fusion protein of the present invention, with or without being complexed to a carrier, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15 edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%. The use of microcapsules or NaNo particules made of polylactide/polyglycolide is also contemplated.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant or other penetration enhancer may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The proteins can also be delivered using implanted mini-pumps, well known in the art.

Furthermore, the proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylaminoethanol, histidine, procaine, or organic salts such as citrate, fumarates, and the like.

To immunize a subject, the polypeptide of interest is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies and the degree of protection desired. With the present vaccine formulations, 0.1 mg of active ingredient per ml of injected solution should be adequate to raise an immunological response when a dose of 1 to 2 ml per animal is administered. Other effective dosages can be readily established by one of ordinary skill in the art through routine trials establishing dose response curves. The subject is immunized by administration of the particular composite or fusion protein in at least one dose, and preferably two doses. Moreover the animal may be administered as many doses as is required to induce potentiating antibodies.

Below are examples of specific embodiments for carrying out the present invention. The examples are offered for illustrative purposes only, and are not intended to limit the scope of the present invention in any way.

EXAMPLE I

This example discloses the design, construction, synthesis, and use of a fusion protein of this invention.

Chemicals and Enzymes

Common chemicals and reagents were purchased from readily available commercial sources. Deoxynucleotide Cyanoethyl Phosphoramidites and DNA synthesis columns were from Applied Biosystems Inc., Foster City, Calif. $T_4$ polynucleotide kinase, $T_4$ DNA ligase and other restriction endonucleases were purchased from Bethesda Research Laboratories and/or New England Biolabs. [γ-$^{32}$P]ATP (4500Ci/mmol) was purchased from ICN Radiochemicals. $^{125}$Iodine was purchased from Amersham. Iodinated Staph A was purchased from New England Nuclear.

Bacterial Strains and Plasmids

E. coli AR58 (galE::TN10, gal1, lambda cI857 deltaH1, Bio⁻uvrB⁻, kil⁻cIII⁻, N99) and AR68 (CAG456::lacAM, trpAM, phoAM, supCTS, strR,HTP⁻, lambdaI857, BAM deltaH1ts, tetR, gal::TN10, Bio⁻, uvrB⁻)(Gross et. al., *Mol. Cell Biol.* 5:1015–1024, (1985)) were used as host for expression of pST epitopes. E. coli MM294 (λC1) was routinely used as a cloning host. Expression plasmids useful for the practice of this invention can be made from publicly available materials by the application of routine non-inventive skill and without the exercise of undue experimentation. Briefly, pAS1 is disclosed in U.S. Pat. No. 4,578,355 and is available from the American Type Culture Collection, Rockville, Md., under accession no. ATCC 39262. A 189bp DpnI fragment containing the 95% efficient $t_o$ terminator from phage λ was purified and inserted into the NroI site of pAS1. This construction is called pOT$_1$ (see also: Devane S. G. et. al., *Cell* 36:43–49 (1984)). pMG27N was derived from pOT$_1$ by digestion of pOT$_1$ with EcoR1 filled in with E. coli DNA polymerase Klenow fragment then partially digested with Bal1. The 5 kilobase EcoR1-Ball fragment, isolated by polyacrylamide gel electrophoresis (PAGE) and electroelecution was incubated overnight with T4 DNA ligase to yield pMG27. Plasmid pMG27 was partially digested with NdeI, filled in, and ligated to yield pMG27N which is characterized by a single NdeI site encompassing an ATG initiation codon located 8 pb downstream of the $C_{II}$ ribosome binding site. (See also: Gross, M. et. al. *Molecular Cell Biol.* 5(5) :1015–24 (1985)). Ten micrograms of pMG27N was digested with restriction endonucleases BamHI and SacI (50 units of each) in 200 μl. medium buffer (described above) for 3 hrs at 37° C.

Ten micrograms of expression vector pAPR801 (Young et. al., *Proc. Natl. Acad. Sci. U.S.A.*, 80:6105 (1983)) containing the influenza virus (A/PR/8/34) non-structural protein 1 (NS1) coding region (Baez, et. al., *Nucleic Acids Research*, 8:5845 (1980)) was digested with restriction endonucleases NcoI and BamHI (20 units each) in 200 μl of high buffer (50 mM Tris-HC1, 1 mM DTT, 10 mM MgCl$_2$ and 100 mM NaCl, pH of 7.5) for 2 hours at 37° C. The resulting 230 base pair fragment, encoding the first 81 N-terminal amino acids of NS1, was isolated by electrophoresis on a 6% polyacrylamide gel (PAGE) and recovered by electroelution.

Forty nanograms of the BamHI/SacI-cut pMG27N (described above) was ligated with 80 ng of the 230 base pair NcoI/BamHI NS1$_{81}$-encoding fragment and 80 ng of a synthetic linker.

The resulting plasmid, pMG-1, was identified with the BamHI site of the NS1$_{81}$ encoding sequence ligated to the BamHI site of pMG27N; the NcoI site of the NS1$_{81}$ encoding sequence ligated to the NcoI site of the synthetic linker; and the SacI site of the synthetic linker ligated to the SacI site of pMG27N.

Of course, genes other than NS1 may be utilized as the fusion partner, inter alia, R32, galK, and β-gal.

The expression plasmid pMG-1 contains the Lambda P$_L$ promoter, cII ribosome binding site and the NS1 gene as a fusion partner. The NS1 gene was modified to insert unique restriction sites immediately following the first 81 amino acids. Using these cloning sites, foreign genes can be inserted in any of the three reading frames at these positions. Downstream of these sites lie termination codons, again in all three frames, to end translation of any fused gene. Plasmid pMG42NS, containing the first 42 amino acids of NS1 as a fusion partner, can also be employed.

Synthesis and Purification of Oligonucleotides

Eight single-stranded deoxyoligonucleotides, ranging in length from 35 to 60 bases, were synthesized on an Applied Biosystems Model 380B DNA synthesizer utilizing phosphoramidate chemistry (Caruthers, *Science* 230:281 (1985)). Each oligonucleotide was purified by electrophoresis through 20% polyacrylamide gels containing 7/M urea. The oligomers were recovered from the gel by electrophoretic transfer onto Whatman DEAE-81 paper followed by elution with 3/M sodium acetate buffer and ethanol precipitation. The sequence of the oligomers was verified by a modification of the Maxam and Gilbert sequencing procedure. (Banaszuk et. al., *Anal. Biochem.* 128:281–286 (1983).)

Construction of pST Synthetic Gene (96–106+33–53+120–150)

Figure 1B:
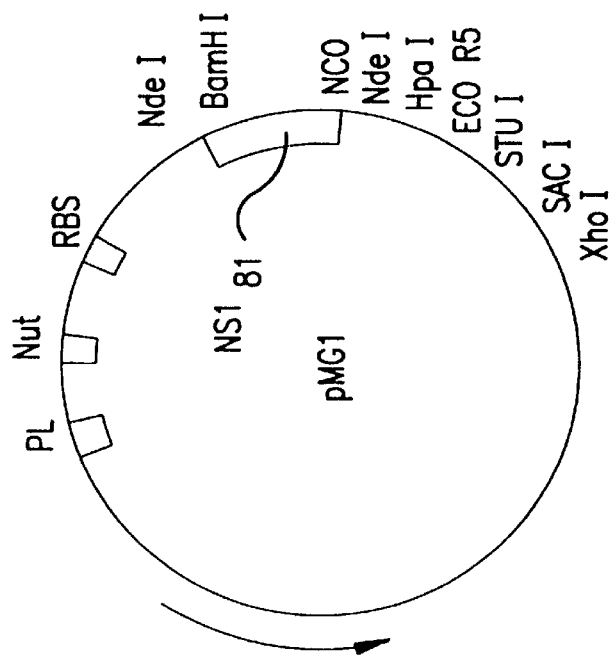

Single-stranded oligonucleotides 2, 3, 4, 5, 6, and 7 (4 μg) (FIG. 1) were phosphorylated at the 5' terminus in a 30 μl reaction mixture containing 50 mM Tris-HCI (pH 7.5), 10 mM MgCl$_2$, 0.1 mM EDTA, 5 mM dithiothreitol, 4 μl [γ-32P]ATP (4500 Ci/mmol) and 20 units of T$_4$ polynucleotide kinase. After incubation at 37° C. for 30 minutes, 1 μl of 10 mM cold ATP was added and the incubation continued for another 30 minutes. The reaction mixture was heated at 65° C. for 10 minutes and the oligonucleotides were ethanol precipitated. Annealing was performed by mixing single-stranded oligonucleotides 2, 3, 5, and 7 with respective complementary single-stranded oligonucleotide 1, 4, 6, and 8 (4 μg each) in a 25 μl reaction mixture containing 10 mM Tris-HCI (pH 7.5) and 100 mM NaCl to form doubled-stranded oligonucleotides with 5'-overhangs of 6–8 bases (FIG. 1). The reaction mixture was heated at 65° C. for 10 minutes and then slowly cooled down to room temperature. The four double-stranded oligonucleotides with complementary single-stranded termini were ligated together to form the synthetic pST epitopes gene in a 50 μl reaction mixture containing 100 pmol of each double-stranded pair in 25 mM Tris-HCl (pH 7.5), 10 mM $MgCl_2$, 2 mM dithiothreitol, 1 mM ATP and 30 units of $T_4$ DNA ligase. Ligation was carried out at 15° C. for 30 hours. Acrylamide gel electrophoresis indicated more than 80% ligation efficiency. [Note that oligonucleotides 1 and 8 were not phosphorylated and left as 5-OH species. Leaving the 5' termini unphosphorylated on these oligonucleotides prevented self-ligation of the final product prior to insertion into the expression vector.] The coding sequence is presented as SEQ ID NO:8.

Cloning of the pST Synthetic Composite Gene in an E. coli Expression Vector

The synthetic composite pST gene was inserted into the bacterial expression vector, pMG-1, as shown in FIG. 1 and described above. The plasmid, pMG-1, is derived from pMG-27 (Gross et. al., supra (1985)) by insertion of a modified DNA sequence encoding the first 81 amino acids of the influenza virus protein, NS1 (Young et. al., *Proc. Nat'l. Acad. Sci.* USA 80:6105–09 (1983)). This vector typically expresses foreign proteins to high levels as fusion polypeptides in *E. coli*. A temperature-sensitive lambda pL promoter drives transcription of the fusion gene and a termination sequence is located downstream of NS1. Expression of foreign genes is inducible in the *E. coli* strain AR58 which contains the temperature-sensitive repressor cl 857 ts (Gross et. al., supra (1985)). Gene expression from this vector is thus controlled by a temperature shift from 32° C. to 42° C. The plasmid also contains an ampicillin resistance to permit selection. Insertion of the synthetic pST epitopes at the EcoRV position in this vector fuses them in frame with the first 81 amino acids of influenza NS1.

20 ng of the synthetic pST composite gene was added to 200 ng of the EcoRV-Xhol digested pNG-1 and ligated as described above for 12 hours with 100 units of $T_4$ DNA ligase in a reaction volume of 20 μl. This cloning fuses the translation frame of the first 81 amino acids of NS1 with the composite PST epitopes. To the ligation mixture 30 μg tRNA was added which was then extracted with phenol and chloroform followed by ethanol precipitation. *E. coli* MM294 λc1+ was transformed with 20 μl of the ligation mixture and plated by serial dilution onto LB medium containing 50 μg/ml ampicillin. Plasmid DNA was prepared from ampicillin-resistant colonies by the alkaline lysis method and screened by digestion with EcoR1 and agarose gel electrophoresis to determine which plasmid DNA had the pST composite gene insert. The sequence of the composite growth hormone gene (FIG. 2) was further verified by dideoxy sequencing procedure (Sanger et. al., *Proc. Nat'l. Acad. Sci.* USA 74:5463–5467 (1977)). Plasmid DNA containing the selected pST epitopes fused to NS1, named pGS81NS1-pST, was then transformed into the AR58 strain for expression studies. The $81NS_1pST$ composite gene sequence is given as SEQ ID NO:3 and the protein encoded thereby as SEQ ID NO:4.

Expression of $81NS_1$-pST Composite Gene

A culture of E. coliAR58 cells harboring the pGS81NS1-pST epitope plasmid was grown in LB medium containing 50 μg/ml ampicillin overnight, diluted 100-fold into the same medium and grown at 32° C. in a 1 Liter shaker flask. When the $A_{650}$ of the culture reached 0.7, expression of the pST composite gene was induced by shifting the temperature from 32° to 42° C. The culture was allowed to grow for an additional 3 hours and then the cells were harvested by centrifugation. A Coomassie stained polyacrylamide protein gel as well as Western blot using antisera against native pST and NS-1 indicated the presence of NS1-pST composite fusion protein at the expected molecular weight (FIG. 2 and 3).

Extraction of NS1/pST composite Fusion Protein from *E. coli*

Two grams of bacterial cell pellet were resuspended in 60 ml of Buffer A (50 mM Tris, pH 7.5, 1 mM EDTA, 1 mM DTT, 5% glycerol) containing 12 mg lysozyme and mixed at room temperature for 30 min. The mixture was transferred to a blender, mixed on ice at high speed for 1–2 min and then sonicated for 1 min. Deoxycholate (600 μl of 10% w/v) was added to the solution which was stirred at 4° C. for 1 h. The solution was then centrifuged at 18,000 rpm for 45 min and the pellet was resuspended in 10 ml of glycine buffer (50 mM glycine-OH, 2 mM EDTA, 5% glycerol). The pellet was sonicated two times for 15 sec. each. More glycine buffer was added (44 mls) with 6 ml of 10% Triton X-1000 and the solution stirred at 4° C. for 1 h. The mixture was centrifuged at 18,000 rpm for 45 min. The pellet was resuspended in 10 ml of Buffer A containing 6 g of urea (3 g urea/g of starting bacterial pellet). This solution was spun at 15,000 rpm for 15–20 min and the supernatant dialyzed against TE buffer overnight. The solution was centrifuged again (10,000 rpm, 10 min) to remove any cloudy precipitate. For pig immunization, this material was further dialyzed against 4 changes of 4 L of $dH_2O$ over 24 h. The dialyzed supernatant was then centrifuged at 10,000 rpm for 30 min prior to use.

Gel Purification of NS1/pST Composite Protein

Approximately 100–200 μl of cell pellet were resuspended in 600 μl Laemmli samples buffer and boiled for 5 min at 100° C. The cell lysate was then electrophoresed on a 17% preparative acrylamide gel (4 mm) along with standard molecular weight markers to trace the fusion protein's position. After electrophoresis, the entire slab gel was placed in ice cold 0.5M KCl to precipitate the protein and the predominant white band of the expected size was excised from the gel. The band was cut into small pieces and placed in an ISCO electroelution apparatus. The inner chamber of the apparatus contained 10 mM Tris acetate, pH 8.6+0.05% SDS. DTT (1 mM, final) was added to the chambers just prior to elution. The samples were subjected to 1–3 watts of constant power for 2–3 h. The concentrated protein was collected by pipet from the inner chamber.

Conjugation of NS1/pST Composite Fusion Protein to Activated BSA

The Imject Activated Supercarrier system (Pierce) was used to conjugate NS1-pST to the carrier protein, BSA, to enhance antibody production following immunization of rabbits. This approach is based on the concept that cationized BSA will carry an antigen that is covalently coupled to it, regardless of size, into the antigen presenting cell (APC) resulting in more efficient processing and presentation of that antigen and consequently yield an enhanced immune response (Muckerheide et. al, *J. Immunol.* 138:833–37 (1987); Apple et. al., *J. Immunol.* 140:3290–95 (1988)). The antigen bound BSA is then mixed with aluminum hydroxide adjuvant followed by injection. The enhanced response of "Supercarrier" conjugated immunogens with this adjuvant can give an antibody titer approximately equal to that seen with incomplete Freund's adjuvant, but without the potential danger to the animal or to the researcher.

The NS1-pST composite fusion protein was coupled to the cationized BSA using manufacturer's instructions. Briefly, one bottle of Purification Salts was dissolved in 60 ml of distilled deionized $H_2O$. Approximately 200 μl containing 500 μg of gel purified NS1-pST composite fusion protein was mixed with 100 μl of conjugation buffer. One 2 mg vial of preactivated carrier protein was dissolved with 200 μl of distilled deionized water and then immediately mixed with the peptide solution. The peptide and activated carrier solution were allowed to react for 2 hours at room temperature. The hapten-carrier conjugate was then purified by gel filtration.

Fractions eluted from the column containing the protein-carrier conjugate were pooled and mixed with alum for 30 min at 4° C. for a final concentration of adjuvant of 1.36 mg/ml. After addition of alum, approximately 45 μg of antigen were administered in 150 μl.

Antibody Production

One rabbit (#12) was immunized with the Imject NS1-pST composite fusion protein conjugated to BSA. Preimmune serum was collected prior to immunization. This rabbit received 150 μl (45 μg) of antigen in each of 5 subcutaneous sites on the back (Day 0). On Day 14, the rabbit was boosted with an equivalent amount of antigen in 3 sites, again subcutaneously. Ten days later (Day 24), the rabbit was bled to measure antibody response to the fusion protein.

Two rabbits (#13, 14) were immunized with the fusion protein in Freund's adjuvant. Preimmune sera was collected prior to immunization. Approximately 150 μg of gel purified NS1-pST composite fusion protein in 1.25 ml was mixed with an equal volume of Complete Freund's adjuvant followed by emulsification. The emulsified material was then used to immunize the rabbits, each animal receiving 0.5 ml (~30 μg at 2 sites subcutaneously on the back (Day 0). The rabbits were boosted 14 days later with ~20 μg of fusion protein emulsified as described above but with Incomplete Freund's adjuvant, administered in 0.5 ml at two subcutaneous sites. The animals were bled on Day 24 to measure antibody response to the fusion protein. Two rabbits (#1, 2) were immunized with pST derived from pig pituitary which had been denatured by boiling for 5 min at 100° C. in Laemmli sample buffer without bromophenol blue dye. The protein was then immediately mixed with Complete Freund's adjuvant and emulsified. Each rabbit received two 0.5 ml subcutaneous injections (~40 μg) on the back (Day 0). The rabbits were boosted on Day 14 with protein prepared as described above and emulsified with Incomplete Freund's adjuvant. Again, the rabbits received two subcutaneous injections of 0.5 ml containing ~40 μg of pST. The animals were bled on Day 21 to measure antibody titer.

ELISA

An ELISA to detect antibodies to pST was developed. Purified native pST (0.1 μg in 100 μl) was adsorbed to the wells of a 96-well immunoassay tray (Nunc, Maxisorp) overnight at 4° C. in 50 mM sodium bicarbonate buffer, pH 9.6. The wells were then washed three times in phosphate-buffered saline +0.05% Tween-20 (PBS-T) and then blocked for 1 h at 37° C. by incubating with 200 μl of 2% BSA in PBS-T. The plates were then washed and 100 μl of rabbit antiserum, diluted in PBS-T, added for 1 h at 37° C. The wells were washed with PBS-T three times and goat anti-rabbit biotin-labeled conjugate (100 μl), diluted 1:1000 in PBS +10% horse serum, was added for 1 h at 37° C. After washing, 100 μl of a streptavidin/peroxidase conjugate (1:1000 in PBS +10% horse serum) was incubated in the wells for 1 h at 37° C. The wells were washed three times and 100 μl of calorimetric substrate (a 1:1 mixture of TMB peroxidase:hydrogen peroxide) was added for 30 min at 37° C. The color reaction was stopped by the addition of 1 M HCl (100 μl) and the absorbance read at 450 mm. Dose response curves were plotted and the titer of the antibody reported as that dilution which gave 50% maximal absorbance.

ELISA to detect reactivity of antibodies to the NS1-pST composite fusion protein have also been performed. The assay follows the protocol described above except that 0.05 μg of the HPLC purified fusion protein, not native pST, is adsorbed to the plates. Reactivity of the antisera to the NS1 moiety alone was determined by measuring binding to an unrelated NS1 fusion protein in an ELISA (0.05 μg of NS1-RLF protein [malaria construct] adsorbed to wells).

Titration of pig sera was performed in the ELISA using the above protocol with the substitution of biotin-conjugated goat anti-swine IgG at 1:2000.

SDS Polyacrylamide Gel Electrophoresis and Western Blot Analysis

Bacterial lysates and/or purified protein were electrophoresed on 15% SDS polyacrylamide gels as described by Laemmli, supra (1970). Prior to electrophoresis the samples were denatured by mixing with sample buffer (0.1 M DTT, 2% SDS, 80 mM Tris, pH 6.8, 10% glycerol, 0.02% bromophenol blue) and boiled for 5 min. at 100° C. Proteins were transferred onto 0.45 μm Immobilon-P (Millipore) for 30 min at 200 mA using a Millipore Milliblot SDE System apparatus according to the manufacturer's directions. The filter was then blocked with 0.5% nonfat dried milk in PBS-T for 1 h at room temperature, rinsed with TTBS (20 mM Tris, pH 7.5, 500 mM NaCl, 0.05% Tween-20), and incubated with polyclonal pST antiserum at a 1:500 dilution in TTBS for 1 h at room temperature. Filters were washed 3×10 min in TTBS and labelled with $^{125}$I-Protein A (Amersham) in TTBS +1% gelatin (1 μCi/10 ml) for 1 h at room temperature. Filters were washed as before, air-dried and exposed to XAR film for various time periods at 70° C.

pST Radioreceptor Assay

Pituitary pST was iodinated to a specific activity of 100 Ci/g using a chloramine-T procedure (Peake, et. al., IN: "Meth. of Hormone Radioimmunoassay" eds. Jaffe and Beheman, Academic Press, p. 229 (1979)) and $^{125}$I-pST was purified on a Biogel P-60 (Biorad) column with 0.05 M phosphate buffered saline, pH 7.2 as the elution buffer. Livers for characterization of pST binding were obtained from Yorkshire barrows (100 kg body weight). The livers were excised, immediately frozen in liquid nitrogen and stored at −70° C. until used. To prepare microsomal membranes for the radioreceptor assay, livers were rapidly thawed at 39° C. in a water bath, finely chopped with scissors, and homogenized with a Polytron homogenizer (Brinkman Instruments, Westbury, N.Y.) for 30 seconds in cold 25 mM Tris-HCl buffer containing 300 mM sucrose, 10 mM aminobenzimidine dihydrochloride and 0.01% thimerosal, pH 9.0, using a tissue weight to buffer volume of 1:5. The homogenate was filtered through eight layers of cheese cloth and centrifuged at 1,900×g for 30 minutes. The supernatant was then filtered through four layers of cheese-cloth and centrifuged at 47,800×g for 90 minutes at 4° C. The pellet from the high speed centrifugation was resuspended by vortexing in 0.05M PBS, pH 7.4 containing 10 mM $CaCl_2$, 0.1% bovine serum albumin (BSA) and 0.01% thimerosal. Prior to the binding assay, the membranes were treated with 4M $MgCl_2$ to remove endogenous pST bound to the receptors. After washing with assay buffer, protein content was determined by Lowry method using BSA as standard. Incubations of microsomal membranes with $^{125}$I-labelled pST in the presence or absence of rabbit antisera were performed at 4° C. as described below. Microsomes and $^{125}$I-pST were diluted in assay buffer (0.05 M PBS pH 7.4, containing 0.01% thimerosal, 10 mM $CaCl_2$, and 0.1% BSA) whereas cold PST and rabbit sera were diluted in 0.05 M PBS pH 7.4 containing 0.1% BSA. Various dilutions of rabbit sera (from 1:500 to 1:50,000) were used. To each assay tube, 100 μl assay buffer was added. This was followed by adding 100 μl of various dilutions of immune rabbit sera or normal rabbit serum (NRS) as a negative control, and 100 μl of $^{125}$I-labelled pST (0.5 to 1 ng, 60,000–80,000 cpm). The tubes were vortexed and incubated for 20 hours at 4° C. The assay was stopped by adding 3.5 ml of cold assay buffer, vortexed, and incubated for 10 minutes. Bound and free hormones were separated by centrifugation at 2,000×g for 30 minutes at 4° C. Non-specific binding was determined by binding of $^{125}$I-labelled pST to microsomes in the presence of 5 μg pituitary pST. Specific binding was measured as the difference between the total and non-specific binding values. In order to determine the effects of the immune rabbit sera on the ability of cold pST to displace $^{125}$I-labelled pST binding to microsomal liver receptors, complexes between the sera (1:100 dilution) and the unlabelled pST (0–50 ng/tube) were preformed 2 hours in advance of incubating with the microsomes. The sera from rabbits immunized against NS1/pST fusion protein was compared against normal rabbit sera and guinea-pig anti-pST antibody run as negative and positive controls, respectively.

Immunoprecipitation of Iodinated pST $^{125}$I-pST (15 μl, prepared as described above) was incubated with preimmune serum (10 μl) and Aprotinin (1 μl of 1:10) in RIPA buffer (85 μl, 1% Triton X-100, 1% Na deoxycholate, 0.1% SDS, 0.15M NaCl, 0.01 M Tris-HCl pH 7.2) for 1 h on ice. Staph A conjugated to Sepharose CL-4B beads (Sigma) was added to the lysates for 30 min at 4° C. and then non-specific immune complexes removed by centrifugation. The clarified supernatants were transferred to a new tube and 10 μl of immune sera was added for 1 h on ice. Staph A Sepharose (100 μl) was added for 2 h on ice and pelleted as above. The immunoprecipitates were washed four times with RIPA buffer and resuspended in 50 μl of Laemmli sample buffer (2% SDS, 0.2M dithiothreitol, 10% glycerol, 0.2% bromophenol blue, 63 mM Tris-HCI, pH 6.8). After boiling for 5 min, the samples were spun in an Eppendorf centrifuge and loaded onto a 15% SDS-polyacrylamide gel as described by Laemmli, supra (1970). $^{14}$C-radiolabeled molecular weight standards were co-electrophoresed on each gel. After electrophoresis, the gels were dried and exposed to Kodak X-Omat AR film at −70° C.

Immunization of Pigs with NS1/pST Composite Protein

Yorkshire-cross barrows, weighing 35 kg at the start of the study, were used for immunization. Pigs were divided into 2 groups of 9 pigs: Group 1 received native NS1/pST in Complete Freund's adjuvant and Group II received SDS-denatured NS1/pST in Freund's adjuvant. Each inoculation consisted of 1 mg of protein in a final volume of 2 ml. Each dose was administered subcutaneously at 4 different sites behind the ears. No injection site was used more than once. The pigs were immunized at day 0, 28 and 49. Sera (10 ml) was collected at various times throughout the immunization regimen by jugular venipuncture. The pigs were carefully observed throughout the vaccination period for health-related problems, specifically the injection sites.

RESULTS

FIG. 2 shows total protein isolated from various transformants.

Lane a: 0 min time sample;

b: induction of 81 NS1 alone at 3 hrs.

c: induction of 81NS1-pST epitope fusion protein;

d: gel purified fusion protein.

The gel was stained using Coomassie blue. Molecular masses of protein standards are shown on FIG. 2. A protein of approx. 15 kDa corresponding to the expected molecular mass of NS1-pST fusion protein was clearly induced. It should be noted in FIG. 2 that there is an apparent induction of several other proteins in addition to the fusion protein. These bands are all bacterial proteins which increase slightly after temperature shift. Nonetheless, the fusion protein is clearly expressed at high level in *E. coli* since it is readily detected by Coomassie blue staining (FIG. 3A).

FIG. 3A illustrates a western blot using NS-1 antiserum. Lanes 1, 2, 5, 6, and 7 contain influenza protein corresponding to 81AA of NS. Lanes 3 and 4 contain 81 NS1-pST fusion proteins. The 81NS1 and fusion proteins were strongly recognized by the NS1 antiserum as expected. It was also recognized by antiserum to influenza NS1 as well as by the antibodies to both denatured native pST and to itself (FIG. 3B). FIG. 3B illustrates a western blot using denatured pST antiserum. Lanes 1, 2, 5, 6, 7, and 8 contain 81 NS-1 proteins which are not recognized by the pST antibody. Lanes 3 and 4 contain 81NS-pST fusion proteins. These proteins are recognized by the pST antiserum. Molecular masses of the protein standards are shown.

Characterization of Antiserum to pST and NS1-pST Fusion Protein

Antibodies were raised in rabbits to both denatured authentic pST as well as to the NS1-pST fusion protein. The antiserum was then analyzed for reactivity to pST by Western, dot blots and ELISA; results are summarized in Table 1. Antisera prepared against denatured authentic pST recognized NS1-pST in bacterial lysates containing the fusion protein on a Western blot. Some higher molecular weight proteins were also recognized by this sera. They may represent multimers of the peptide not fully dissociated by the SDS sample buffer.

TABLE 1

Summary of Biological Activity of Sera Prepared Against pST of NS1-pST Fusion Protein

| Rabbit Immunogen # | ELISA Titer | Reactivity to pST by: | | | |
|---|---|---|---|---|---|
| | | Western | Dot | Ippt | RRA |
| 1 denatured pST (04/23/90) | 1:18,900 | +++ | ++ | +++ | NT* |
| 2 denatured pST (10/10/90) | 1:10,200 | ++ | + | + | NT |
| 12 NS1-pST conjugated to BSA (10/10/90) | 1:4,830 | ++ | ++ | + | no |
| 13 NS1-pST + Freund's adjuvant (10/10/90) | 1:1,730,000 | +++ | ++ | +++ | no |
| 14 NS1-pST + Freund's adjuvant (10/10/90) | <1:1,000 | ++ | + | + | no |
| guinea pig native pST | 1:6,310 | NT | NT | +++ | yes |

*Not Tested

Antiserum from those rabbits immunized with gel purified NS1-pST fusion protein recognized both the fusion protein as well as denatured authentic pST when analyzed by Western. The level of reactivity was dependent on the rabbit. For example, one rabbit produced antiserum which strongly recognized both the fusion protein and denatured pST while another serum only recognized the NS1-pST composite fusion protein. The antibodies from all 3 rabbits also recognized NS1 alone, indicating that some of the reactivity was directed to the NS1 portion of the molecule.

The antisera were also characterized by dot blot. Authentic pST was dotted onto nitrocellulose membranes and then probed with the rabbit α pST serum. Again, the level of reactivity to pST was dependent on the rabbit used to produce antiserum and was consistent with the results observed by Western.

The rabbit antibodies were tested in an ELISA where authentic pST had been adsorbed to 96-well trays. Titrations were performed across a series of antibody dilutions and titers are reported as the dilution giving 50% maximal adsorption in the ELISA. In this assay, all serum tested showed reactivity with authentic pST. The titer of the antibodies to pST was well-predicted by their Western reactivity. Rabbit #1 and #13 had the highest titer to authentic pST while those sera which did not detect pST by Western or dot blot analysis were found to contain a low but reproducible level of anti-pST reactivity.

The ability of the NS1-pST fusion protein to elicit antibodies in the target species, swine, was also investigated. Pigs were immunized with "native" or denatured NS1-pST fusion protein, administered subcutaneously four times, 1 mg per dose. Seroconversion was monitored by ELISA. After 2 immunizations, sera from the immunized swine, regardless of the nature of the immunogen, i.e., native or denatured, showed reactivity in an ELISA to authentic pST (Table 2) and NSl-pST (Table 3). A proportion of these antibodies recognized the NS1 moiety of the fusion protein in that an unrelated NS1 fusion protein, NS1-RLF (malaria construct) was also recognized by the pig sera in an ELISA (Table 3). Preimmune pig sera had little or no titer to any of the proteins tested in ELISA. Sera from immunized pigs also detected pST, NS1-pST and NS1-RLF when subjected to Western analysis.

TABLE 2

Titration of Sera from Pigs Immunized with NS1-pST in pST ELISA

| Pig # | Reciprocal Titer: Preimmune | 03/28/91 | 04/18/91 | 04/25/91 | 05/09/91 | 06/13/91 |
|---|---|---|---|---|---|---|
| Native NS1/pST | | | | | | |
| 358 | 1,930 | 14,200 | 6,090 | — | 40,500 | NT* |
| 359 | 297 | 1,770 | — | 1,560 | 12,100 | NT |
| 361 | 1,000 | 17,800 | — | — | >60,000 | NT |
| 362 | NA | — | — | — | 16,400 | NT |
| 363 | <10 | 16,800 | 21,800 | — | >60,000 | NT |
| 364 | 10 | 7,520 | 4,000 | — | 33,400 | NT |
| 365 | <10 | 26,300 | 4,380 | — | 62,300 | NT |
| 366 | <10 | 3,850 | 520 | — | 5,390 | NT |
| 367 | 160 | 40 | 25,200 | — | >61,400 | NT |
| Denatured pST | | | | | | |
| 368 | 2,620 | 42,400 | 26,000 | — | 50,700 | 6,430 |
| 369 | <10 | 8,630 | 25,900 | — | 38,200 | 15,260 |
| 370 | 200 | 22,800 | 8,830 | — | 21,200 | NT |
| 371 | 520 | 21,500 | 28,100 | — | >60,000 | 6,060 |
| 372 | <10 | 26,200 | 30,200 | — | >20,000 | 2,260 |
| 374 | <10 | 15,600 | 25,700 | — | >74,200 | 30,400 |

*Not Tested

TABLE 3

ELISA Titration of Sera from Swine Immunized with NS1-pST

Reciprocal Dilution of Sera Titered Against

| Pig # | pST 05/09/91 | pST 06/13/91 | NS1 05/09/91 | NS1 06/13/91 | NS1-pST 05/09/91 | NS1-pST 06/13/91 |
|---|---|---|---|---|---|---|
| 368 | 25,800 | 6,430 | 147,800 | 77,400 | 439,000 | 160,000 |
| 369 | 17,800 | 15,260 | 123,600 | 195,600 | 206,000 | 400,000 |
| 371 | 37,200 | 6,060 | 156,400 | 60,600 | 293,000 | 107,000 |
| 372 | 1,308 | 2,260 | 31,400 | 55,400 | 52,500 | 114,000 |
| 374 | 25,000 | 30,400 | 74,800 | 83,000 | 93,800 | 103,000 | pST adsorbed to plates at 100 ng/well; NS1-RLF (malaria fusion protein) and NS1-pST adsorbed to plates at 50 ng/well.

Immunoprecipitation (Ippt) of Iodinated pST ($^{125}$I-pST)

The rabbit antibodies to denatured pST and to the NS1-pST composite fusion protein were used to immunoprecipitate iodinated 22K pST (FIG. 4). As a control, $^{125}$I-pST was reacted with antibodies produced in guinea pigs to native pST. A 22 kD protein was precipitated by the antibodies to native pST at both dilutions tested (1:500 and 1:1000). Antibodies from rabbits #1 and #13, which had high ELISA titers, immunoprecipitated the same 22 kD protein when used at 1:10 but not 1:500 dilution. The other rabbit antibodies precipitated little or no pST even at the lowest dilution; the ELISA titers of these sera were also low. These results indicate that antibodies to denatured pST or to the composite fusion protein expressing selected epitopes of the hormone can detect native pST in solution but these sera are not as efficient at immunoprecipitation as those antibodies prepared to native pST. Of course, sera from rabbits immunized with the NSl-pST fusion protein recognize only 3 regions of the hormone in contrast to sera raised against the entire pST molecule.

Sera from pigs immunized with the NS1-pST fusion protein were also tested for their ability to immunoprecipitate $^{125}$I-pST (FIG. 6). As observed previously, antibodies from guinea pigs immunized with native pST immunoprecipitated 22K pST in this assay as did sera from rabbit #13 immunized with NS1-pST. Preimmune serum from pigs did not recognize the iodinated hormone, but after immunization, sera from pigs vaccinated with either "native" NS1-pST (#365) or denatured NS1-pST (#731) immunoprecipitated $^{125}$I-pST. These results demonstrate that in the target animal, swine, immunization with NS1-pST produces an antibody response to the fusion protein which recognizes native pST.

RadioReceptor Assay

Since antibodies to the NS1-pST fusion protein immunoprecipitated pST, the antisera were used in a radio-receptor assay to determine if it would interfere with the binding of native pST to its receptor. Various dilutions of the rabbit sera α NS1-pST were incubated with liver membranes isolated from cells expressing the growth hormone receptor for 20 hours at 4° C. in the presence of $^{125}$I-pST. The amount of radiolabeled pST associated with the membrane fraction is then determined. Antibody prepared in guinea pigs against native pST effectively removed the ability of all levels of unlabelled pST to displace $^{125}$I-pST binding, indicating that this antibody binds to epitopes on pST that are associated with receptor binding. The concentrations of unlabelled pST used in the binding assays correspond to the range of pST normally found in the plasma of pigs. In contrast, binding of $^{125}$I-pST to the liver receptors was not affected by any of the rabbit sera prepared to the composite fusion protein (Table 4). Normal rabbit serum also failed to prevent the binding of $^{125}$I-pST to microsomal receptors.

TABLE 4

Effect of Rabbit Sera on the Binding of $^{125}$I-pST to Liver Microsomal Membranes

| | % BINDING Dilution | | | | |
|---|---|---|---|---|---|
| | 1:500 | 1:1000 | 1:5000 | 1:10000 | 1:50000 |
| Rabbit #12 | 11.62 | 12.90 | 12.29 | 12.00 | 13.52 |
| Rabbit #13 | 12.18 | 12.76 | 13.12 | 13.28 | 12.02 |
| Rabbit #14 | 10.97 | 12.49 | 11.28 | 11.51 | 12.28 |
| Normal Rabbit Serum | 13.04 | 12.55 | 12.52 | 12.28 | 12.92 |
| Guinea Pig α native pST | — | — | 3.72 | — | 4.29 |

Various dilutions of sera were incubated with membranes for 20 hours at 4° C. in the presence of $^{125}$I-pST. The values are specific binding expressed as a percentage of total radioactivity from three separate experiments.

Effects of rabbit antisera (1:1000) on the ability of increasing concentrations of unlabelled pST to displace $^{125}$I-pST binding to liver membranes is shown in FIG. 5. Controls used were normal rabbit serum (NRS), assay buffer, and guinea pig antibody to native pST (1:1000). Complexes formed by the antibodies and various levels of unlabelled hormone continued to displace 125I-pST binding to liver receptors. The ability of these antibodies to bind to authentic pST but their failure to prevent interaction of pST with its receptor suggests that these antibodies may increase the half-life of the pST in circulation.

Sera from pigs immunized with NS1-pST fusion protein were also tested for their effects on the binding of $^{125}$I-pST in the presence of various concentrations of unlabelled pST. Sera were obtained from pigs immunized with "native" NS1-pST fusion protein (pigs #365 and 367) or protein denatured with 0.1% SDS (pigs #371 and 374). The sera were tested at 1:1000 dilution in 0.1M phosphate buffered saline containing 0.1% bovine serum albumin (PBS/BSA). The diluted sera or controls (normal pig sera, PBS buffer and guinea pig anti-pST antibody) were incubated for two hours with various concentrations 0–100 ng/tube) of pST at room temperature. Two hundred microliters of the mixture were added (in triplicates) to tubes containing liver microsomal membranes (200 μg protein) and $^{125}$I-pST (60–80,000 cpm) in assay buffer. Each serum was tested in preparations of liver membranes obtained from at least two untreated pigs. The tubes were vortexed and incubated 20 hours at 4° C. The assay was stopped by adding cold assay buffer (3.0. ml), vortexed and incubated for a further 10–15 minutes. Bound and free were separated by centrifugation at 2,000×g for 30 minutes at 4° C. and counted in a gamma counter.

Effects of sera from immunized pigs on the ability of increasing concentrations of unlabelled pST to displace $^{125}$I-pST binding to liver membranes are shown in FIG. 7. Controls used were normal pig sera (NPS), assay buffer (PBS), and guinea pig antibody (GP AB) to pST (1:1000).

Results show that the sera from the immunized pigs did not prevent various concentrations of unlabelled pST from displacing $^{125}$I-pST binding to liver membranes. Similar effects were observed when incubations were performed in normal pig serum or assay buffer. However, preincubation with guinea pig antibody to pST eliminated virtually all of the ability of the unlabelled pST to displace $^{125}$I-pST binding, demonstrating that this antibody binds to the receptor binding domains of pST. In contrast, antibodies produced in the pigs following immunization with "native" or denatured NS1-pST fusion protein did not prevent displacement of $^{125}$I-pST by unlabelled pST, indicating that epitopes involved in the binding to liver receptors were not affected. Thus, antibodies produced in pigs following immunization with the selected epitopes do not interfere with hormone-receptor binding and its biological functions.

What is claimed is:

1. A composite peptide comprising at least two non-contiguous somatotropin epitopic amino acid sequences, wherein said composite peptide is substantially free of receptor binding domain sequences.

2. The composite peptide according to claim 1 comprising at least three non-contiguous somatotropin epitopic amino acid sequences.

3. The composite peptide according to claim 1 comprising at least four non-contiguous somatotropin epitopic amino acid sequences.

4. The composite peptide according to claim 1 wherein said epitopic amino acid sequences are selected from the group consisting of 33–53pST$_{190}$ (SEQ ID NO:5), 35–53pST$_{191}$ (SEQ ID NO:6), 35–43pST$_{191}$ (SEQ ID NO:7), 35–48pST$_{191}$ (SEQ ID NO:10), 96–106pST$_{190}$ (SEQ ID NO:11), 98–110pST$_{191}$ (SEQ ID NO:12), 110–118pST$_{191}$ (SEQ ID NO:13), 119–131pST$_{191}$ (SEQ ID NO:14), 120–140pST$_{191}$ (SEQ ID NO:15), 120–150pST$_{190}$ (SEQ ID NO:16), 122–138pST$_{191}$ (SEQ ID NO:17), 123–137pST$_{191}$ (SEQ ID NO:18), 130–143pST$_{191}$ (SEQ ID NO:19), 133–146pST$_{191}$ (SEQ ID NO:20), 134–154pST$_{191}$ (SEQ ID NO:21), 155–163pST$_{191}$ (SEQ ID NO:22), and immunogenic fragments thereof.

5. The composite peptide according to claim 4 wherein said epitopic sequences are 33–53pST$_{190}$ (SEQ ID NO:5), 96–106pST$_{190}$ (SEQ ID NO:11), and 120–150pST$_{190}$ (SEQ ID NO:16) and immunogenic fragments thereof.

6. The composite peptide according to claim 5 having sequence NH$_2$-96–106pST$_{190}$,-33–53pST$_{190}$-120–150pST$_{190}$-COOH (SEQ ID NO:9).

7. A fusion protein comprising a composite somatotropin peptide linked to a heterologous protein, wherein said composite peptide is substantially free of receptor binding domain sequences.

8. The fusion protein according to claim 7 wherein said composite protein is NH$_2$-96–106pST$_{190}$-33–53pST$_{190}$-120–150pST$_{190}$-COOH (SEQ ID NO:9).

9. The fusion protein according to claim 7 wherein the heterologous protein is selected from the group consisting of β-galactosidase, influenza nonstructural protein (NS1), R32, galK, and fragments thereof.

10. The fusion protein according to claim 9 wherein said heterologous protein is influenza protein NS1 or fragment thereof.

11. The fusion protein according to claim 10 wherein the heterologous protein is an 81 amino acid NH$_2$ terminal fragment of influenza protein NS1.

12. The fusion protein according to claim 7 wherein the composite peptide is NH$_2$-96–106pST$_{190}$-33–53pST$_{190}$-120–150pST$_{190}$-COOH (SEQ ID NO:9) and the heterologous protein is an 81 amino acid NH$_2$-terminal fragment of influenza protein NS1.

13. The composite peptide according to claim 1 linked to a carrier by chemical cross-linking.

14. The fusion protein according to claim 7 linked to a carrier by chemical cross-linking.

15. The fusion protein according to claim 14 wherein said carrier is selected from the group consisting of serum albumin, myoglobin, bacterial toxoids, and keyhole limpet haemocyanin.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 633 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Sus scrofa
        ( F ) TISSUE TYPE: Pituitary gland ( v i i ) IMMEDIATE SOURCE:
        ( B ) CLONE: pGH-1/pGH-2

( x i ) SEQUENCE DESCRIPTION: SEQ ID NO:1:

```
ACCTCCGTGC  TCCTGGCTTT  CGCCCTGCTC  TGCCTGCCCT  GGACTCAGGA  GGTGGGAGCC      60
TTCCCAGCCA  TGCCCTTGTC  CAGCCTATTT  GCCAACGCCG  TGCTCCGGGC  CCAGCACCTG     120
CACCAACTGG  CTGCCGACAC  CTACAAGGAG  TTTGAGCGCG  CCTACATCCC  GGAGGGACAG     180
AGGTACTCCA  TCCAGAACGC  CCAGGCTGCC  TTCTGCTTCT  CGGAGACCAT  CCCGGCCCCC     240
ACGGGCAAGG  ACGAGGCCCA  GCAGAGATCG  GACGTGGAGC  TGCTGCGCTT  CTCGCTGCTG     300
CTCATCCAGT  CGTGGCTCGG  GCCCGTGCAG  TTCCTCAGCA  GGGTCTTCAC  CAACAGCCTG     360
GTGTTTGGCA  CCTCAGACCG  CGTCTACGAG  AAGCTGAAGG  ACCTGGAGGA  GGGCATCCAG     420
GCCCTGATGC  GGGAGCTGGA  AGATGGCAGC  CCCCGGGCAG  GACAGATCCT  CAAGCAAACC     480
TACGACAAAT  TTGACACAAA  CTTGCGCAGT  GATGACGCGC  TGCTTAAGAA  CTACGGGCTG     540
CTCTCCTGCT  TCAAGAAGGA  CCTGCACAAG  GCTGAGACAT  ACCTGCGGGT  CATGAAGTGT     600
CGCCGCTTCG  TGGAGAGCAG  CTGTGCCTTC  TAG                                    633
```

( 2 ) INFORMATION FOR SEQ ID NO:2:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

| Phe | Pro | Ala | Met | Pro | Leu | Ser | Ser | Leu | Phe | Ala | Asn | Ala | Val | Leu | Arg |
| 1 | | | | 5 | | | | | 10 | | | | | 15 | |

| Ala | Gln | His | Leu | His | Gln | Leu | Ala | Ala | Asp | Thr | Tyr | Lys | Glu | Phe | Glu |
| | | | 20 | | | | | 25 | | | | | 30 | | |

| Arg | Ala | Tyr | Ile | Pro | Glu | Gly | Gln | Arg | Tyr | Ser | Ile | Gln | Asn | Ala | Gln |
| | | 35 | | | | | 40 | | | | | 45 | | | |

| Ala | Ala | Phe | Cys | Phe | Ser | Glu | Thr | Ile | Pro | Ala | Pro | Thr | Gly | Lys | Asp |
| | 50 | | | | | 55 | | | | | 60 | | | | |

| Glu | Ala | Gln | Gln | Arg | Ser | Asp | Val | Glu | Leu | Leu | Arg | Phe | Ser | Leu | Leu |
| 65 | | | | | 70 | | | | | 75 | | | | | 80 |

| Leu | Ile | Gln | Ser | Trp | Leu | Gly | Pro | Val | Gln | Phe | Leu | Ser | Arg | Val | Phe |
| | | | | 85 | | | | | 90 | | | | | 95 | |

| Thr | Asn | Ser | Leu | Val | Phe | Gly | Thr | Ser | Asp | Arg | Val | Tyr | Glu | Lys | Leu |
| | | | 100 | | | | | 105 | | | | | 110 | | |

| Lys | Asp | Leu | Glu | Glu | Gly | Ile | Gln | Ala | Leu | Met | Arg | Glu | Leu | Glu | Asp |
| | | 115 | | | | | 120 | | | | | 125 | | | |

| Gly | Ser | Pro | Arg | Ala | Gly | Gln | Ile | Leu | Lys | Gln | Thr | Tyr | Asp | Lys | Phe |
| | 130 | | | | | 135 | | | | | 140 | | | | |

| Asp | Thr | Asn | Leu | Arg | Ser | Asp | Ala | Leu | Leu | Lys | Asn | Tyr | Gly | Leu |
| 145 | | | | | 150 | | | | | 155 | | | | 160 |

| Leu | Ser | Cys | Phe | Lys | Lys | Asp | Leu | His | Lys | Ala | Glu | Thr | Tyr | Leu | Arg |
| | | | | 165 | | | | | 170 | | | | | 175 | |

| Val | Met | Lys | Cys | Arg | Arg | Phe | Val | Glu | Ser | Ser | Cys | Ala | Phe |
| | | | 180 | | | | | 185 | | | | | 190 |

( 2 ) INFORMATION FOR SEQ ID NO:3:

( i ) SEQUENCE CHARACTERISTICS:
        ( A ) LENGTH: 453 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Sus scrofa ( x i ) SEQUENCE DESCRIPTION: SEQ ID NO:3:

```
ATGGATCCAA ACACTGTGTC AAGCTTTCAG GTAGATTGCT TTCTTTGGCA TGTCCGCAAA        60
CGAGTTGCAG ACCAAGAACT AGGTGATGCC CCATTCCTTG ATCGGCTTCG CCGAGATCAG       120
AAATCCCTAA GAGGAAGGGG CAGCACTCTT GGTCTGGACA TCGAGACAGC CACACGTGCT       180
GGAAAGCAGA TAGTGGAGCG GATTCTGAAA GAAGAATCCG ATGAGGCACT TAAAATGACC       240
ATGGATCATA TGTTAACAGA TTTTACGAAT TCCCTGGTTT TTGGCACATC CGACAGAGCA       300
TATATTCCCG AAGGCCAGCG TTATTCCATT CAGAATGCAC AGGCAGCATT TTGTTTCCAG       360
GCACTGATGA GAGAACTGGA AGACGGATCC CCCAGAGCAG GCCAGATTCT GAAACAGACA       420
TATGACAAAT TTGACACAAA CCTGAGATCC TGA                                   453
```

( 2 ) INFORMATION FOR SEQ ID NO:4:

( i ) SEQUENCE CHARACTERISTICS:
  ( A ) LENGTH: 150 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
  ( A ) ORGANISM: Sus scrofa ( x i ) SEQUENCE DESCRIPTION: SEQ ID NO:4:

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
                20                  25                  30

Leu Asp Arg Leu Arg Arg Asp Gln Asn Ser Leu Arg Gly Arg Gly Ser
            35                  40                  45

Thr Leu Gly Leu Asp Ile Glu Thr Ala Thr Arg Ala Gly Lys Gln Ile
        50                  55                  60

Val Glu Arg Ile Leu Lys Glu Glu Ser Asp Glu Ala Leu Lys Met Thr
65                  70                  75                  80

Met Asp His Met Leu Thr Asp Phe Thr Asn Ser Leu Val Phe Arg Thr
                85                  90                  95

Ser Asp Arg Ala Tyr Ile Pro Glu Gly Gln Arg Tyr Ser Ile Gln Asn
                100                 105                 110

Ala Gln Ala Ala Phe Cys Phe Gln Ala Leu Met Arg Glu Leu Glu Asp
            115                 120                 125

Gly Ser Pro Arg Ala Gly Gln Ile Leu Lys Gln Thr Tyr Asp Lys Phe
        130                 135                 140

Asp Thr Asn Leu Arg Ser
145                 150
```

( 2 ) INFORMATION FOR SEQ ID NO:5:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Sus scrofa ( i x ) FEATURE:
    ( A ) NAME/KEY: Peptide
    ( B ) LOCATION: 1..21
    ( D ) OTHER INFORMATION: /note= ""REPRESENTS RESIDUES 33-53
        OF PST1- 190""

( x i ) SEQUENCE DESCRIPTION: SEQ ID NO:5:

```
Arg Ala Tyr Ile Pro Glu Gly Gln Arg Tyr Ser Ile Gln Asn Ala Gln
1               5                   10                  15
```

```
Ala  Ala  Phe  Cys  Phe
              20
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Sus scrofa ( i x ) FEATURE:
        ( A ) NAME/KEY: Peptide
        ( B ) LOCATION: 1..19
        ( D ) OTHER INFORMATION: /note= ""THIS PEPTIDE REPRESENTS RESIDUES 35- 53 OF PST1-191""

( x i ) SEQUENCE DESCRIPTION: SEQ ID NO:6:

```
Ala  Tyr  Ile  Pro  Glu  Gly  Gln  Arg  Tyr  Ser  Ile  Gln  Asn  Ala  Asn  Ala
1                   5                             10                  15
Ala  Phe  Cys
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Sus scrofa ( i x ) FEATURE:
        ( A ) NAME/KEY: Peptide
        ( B ) LOCATION: 1..9
        ( D ) OTHER INFORMATION: /note= ""THIS PEPTIDE REPRESENTS RESIDUES 35- 43 OF PST1-191""

( x i ) SEQUENCE DESCRIPTION: SEQ ID NO:7:

```
Ala  Tyr  Ile  Pro  Glu  Gly  Gln  Arg  Tyr
1                   5
```

( 2 ) INFORMATION FOR SEQ ID NO:8:

( i ) SEQUENCE CHARACTERISTICS:
        ( A ) LENGTH: 192 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Sus scrofa
    ( F ) TISSUE TYPE: Pituitary gland ( x i ) SEQUENCE DESCRIPTION: SEQ ID NO:8:

```
TTTACGAATT CCCTGGTTTT TGGCACATCC GACAGAGCAT ATATTCCCGA AGGCCAGCGT     60
TATTCCATTC AGAATGCACA GGCAGCATTT TGTTTCCAGG CACTGATGAG AGAACTGGAA    120
GACGGATCCC CCAGAGCAGG CCAGATTCTG AAACAGACAT ATGACAAATT TGACACAAAC    180
CTGAGATCCT GA                                                       192
```

( 2 ) INFORMATION FOR SEQ ID NO:9:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Phe Thr Asn Ser Leu Val Phe Gly Thr Ser Asp Arg Ala Tyr Ile Pro
 1               5                  10                  15
Glu Gly Gln Arg Tyr Ser Ile Gln Asn Ala Gln Ala Ala Phe Cys Phe
            20                  25                  30
Gln Ala Leu Met Arg Glu Leu Glu Asp Gly Ser Pro Arg Ala Gly Gln
        35                  40                  45
Ile Leu Lys Gln Thr Tyr Asp Lys Phe Asp Thr Asn Leu Arg Ser
    50                  55                  60
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Sus scrofa ( i x ) FEATURE:
        ( A ) NAME/KEY: Peptide
        ( B ) LOCATION: 1..14
        ( D ) OTHER INFORMATION: /note= ""THIS PEPTIDE REPRESENTS
        RESIDUES 35- 48 OF PST1-191""

( x i ) SEQUENCE DESCRIPTION: SEQ ID NO:10:

```
Ala Tyr Ile Pro Glu Gly Gln Arg Tyr Ser Ile Gln Asn Ala
 1               5                  10
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Sus Scrofa (i x) FEATURE:
    (A) NAME/KEY: Peptide
    (B) LOCATION: 1..11
    (D) OTHER INFORMATION: /note= "THIS PEPTIDE REPRESENTS
        REPRESENTS RESIDUES 96-106 OF PST1-190"

(x i) SEQUENCE DESCRIPTION: SEQ ID NO:11:

```
Phe Thr Asn Ser Leu Val Phe Gly Thr Ser Asp
1               5                   10
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
        (A) ORGANISM: Sus scrofa (i x) FEATURE:
        (A) NAME/KEY: Peptide
        (B) LOCATION: 1..13
        (D) OTHER INFORMATION: /note= ""THIS PEPTIDE REPRESENTS
            RESIDUES 98- 110 OF PST1-191""

(x i) SEQUENCE DESCRIPTION: SEQ ID NO:12:

```
Thr Asn Ser Leu Val Phe Gly Thr Ser Asp Arg Val Tyr
1               5                   10
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
        (A) ORGANISM: Sus Scrofa (i x) FEATURE:
        (A) NAME/KEY: Peptide
        (B) LOCATION: 1..9
        (D) OTHER INFORMATION: /note= ""THIS PEPTIDE REPRESENTS
            RESIDUES 110- 118 OF PST1-191""

(xi) SEQUENCE DESCRIPTION: SEQ ID NO:13:

Tyr Glu Lys Leu Lys Asp Leu Glu Glu
1               5

(2) INFORMATION FOR SEQ ID NO:14:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
      (A) ORGANISM: Sus scrofa (ix) FEATURE:
      (A) NAME/KEY: Peptide
      (B) LOCATION: 1..13
      (D) OTHER INFORMATION: /note= ""THIS PEPTIDE REPRESENTS
          RESIDUES 119- 131 OF PST1-191""

(xi) SEQUENCE DESCRIPTION: SEQ ID NO:14:

Gly Ile Gln Ala Leu Met Arg Glu Leu Glu Asp Gly Ser
1               5                   10

(2) INFORMATION FOR SEQ ID NO:15:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
      (A) ORGANISM: Sus scrofa (ix) FEATURE:
      (A) NAME/KEY: Peptide
      (B) LOCATION: 1..21
      (D) OTHER INFORMATION: /note= ""THIS PEPTIDE REPRESENTS
          RESIDUES 120- 140 OF PST1-191""

(xi) SEQUENCE DESCRIPTION: SEQ ID NO:15:

Ile Gln Ala Leu Met Arg Glu Leu Glu Asp Gly Ser Pro Arg Ala Gly
1               5                   10                  15

Gln Ile Leu Lys Gln
            20

(2) INFORMATION FOR SEQ ID NO:16:

(i) SEQUENCE CHARACTERISTICS:
      (A) LENGTH: 31 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
   (A) ORGANISM: Sus Scrofa (ix) FEATURE:
   (A) NAME/KEY: Peptide
   (B) LOCATION: 1..31
   (D) OTHER INFORMATION: /note= ""THIS PEPTIDE REPRESENTS RESIDUES 120- 150 OF PST1-190""

(xi) SEQUENCE DESCRIPTION: SEQ ID NO:16:

Gln Ala Leu Met Arg Glu Leu Glu Asp Gly Ser Pro Arg Ala Gly Gln
1               5                   10                  15

Ile Leu Lys Gln Thr Tyr Asp Leu Phe Asp Thr Asn Leu Arg Ser
            20                  25                  30

(2) INFORMATION FOR SEQ ID NO:17:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:
      (A) ORGANISM: Sus scrofa (ix) FEATURE:
      (A) NAME/KEY: Peptide
      (B) LOCATION: 1..17
      (D) OTHER INFORMATION: /note= ""THIS PEPTIDE REPRESENTS RESIDUES 122- 138 OF PST1-191""

(xi) SEQUENCE DESCRIPTION: SEQ ID NO:17:

Ala Leu Met Arg Glu Leu Glu Asp Gly Ser Pro Arg Ala Gly Gln Ile
1               5                   10                  15

Leu (2) INFORMATION FOR SEQ ID NO:18:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
      (A) ORGANISM: Sus scrofa (ix) FEATURE:
      (A) NAME/KEY: Peptide
      (B) LOCATION: 1..15

(D) OTHER INFORMATION: /note= ""THIS PEPTIDE REPRESENTS
RESIDUES 123- 137 OF PST1-191""

(x i) SEQUENCE DESCRIPTION: SEQ ID NO:18:

Leu Met Arg Glu Leu Glu Asp Gly Ser Pro Arg Ala Gly Gln Ile
1               5                   10                  15

(2) INFORMATION FOR SEQ ID NO:19:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
      (A) ORGANISM: Sus scrofa (x i) SEQUENCE DESCRIPTION: SEQ ID NO:19:

Gly Ser Pro Arg Ala Gly Gln Ile Leu Lys Gln Thr Tyr Asp
1               5                   10

(2) INFORMATION FOR SEQ ID NO:20:

(i) SEQUENCE CHARACTERISTICS:
      (A) LENGTH: 14 amino acids
      (B) TYPE: amino acid
      (C) STRANDEDNESS: single
      (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
      (A) ORGANISM: Sus scrofa (i x) FEATURE:
      (A) NAME/KEY: Peptide
      (B) LOCATION: 1..14
      (D) OTHER INFORMATION: /note= ""THIS PEPTIDE REPRESENTS
         AMINO ACID RESIDUES 133-146 OF PST1-191""

(x i) SEQUENCE DESCRIPTION: SEQ ID NO:20:

Arg Ala Gly Gln Ile Leu Tyr Gln Thr Tyr Asp Lys Phe Asp
1               5                   10

(2) INFORMATION FOR SEQ ID NO:21:

(i) SEQUENCE CHARACTERISTICS:
      (A) LENGTH: 21 amino acids
      (B) TYPE: amino acid
      (C) STRANDEDNESS: single
      (D) TOPOLOGY: linear (i i) MOLECULE TYPE: peptide (i i i) HYPOTHETICAL: NO (i v) ANTI-SENSE: NO (v) FRAGMENT TYPE: internal ( v i ) ORIGINAL SOURCE:
    ( A ) ORGANISM: Sus scrofa ( i x ) FEATURE:
    ( A ) NAME/KEY: Peptide
    ( B ) LOCATION: 1..21
    ( D ) OTHER INFORMATION: /note= ""THIS PEPTIDE REPRESENTS AMINO ACID RESIDUES 134-154 OF PST1-191""

( x i ) SEQUENCE DESCRIPTION: SEQ ID NO:21:

```
Ala Gly Gln Ile Leu Lys Gln Thr Tyr Asp Lys Phe Asp Thr Asn Leu
1               5                   10                  15
Arg Ser Asp Asp Ala
            20
```

( 2 ) INFORMATION FOR SEQ ID NO:22:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Sus scrofa ( i x ) FEATURE:
    ( A ) NAME/KEY: Peptide
    ( B ) LOCATION: 1..9
    ( D ) OTHER INFORMATION: /note= ""THIS PEPTIDE REPRESENTS AMINIO ACID RESIDUES 155-163 OF PST1-191""

( x i ) SEQUENCE DESCRIPTION: SEQ ID NO:22:

```
Leu Leu Lys Asn Tyr Gly Leu Leu Ser
1               5
```

( 2 ) INFORMATION FOR SEQ ID NO:23:

( i ) SEQUENCE CHARACTERISTICS:
    ( A ) LENGTH: 196 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Sus scrofa
    ( F ) TISSUE TYPE: Pituitary gland ( x i ) SEQUENCE DESCRIPTION: SEQ ID NO:23:

```
TTTACGAATT CCCTGGTTTT TGGCACATCC GACAGAGCAT ATATTCCCGA AGGCCAGCGT      60
TATTCCATTC AGAATGCACA GGCAGCATTT TGTTTCCAGG CACTGATGAG AGAACTGGAA     120
GACGGATCCC CCAGAGCAGG CCAGATTCTG AAACAGACAT ATGACAAATT TGACACAAAC     180
CTGAGATCCT GATAAC                                                     196
```

( 2 ) INFORMATION FOR SEQ ID NO:24:

(i) SEQUENCE CHARACTERISTICS:
    (A) LENGTH: 200 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Sus scrofa
    (F) TISSUE TYPE: Pituitary gland (xi) SEQUENCE DESCRIPTION: SEQ ID NO:24:

| | | | | | | |
|---|---|---|---|---|---|---|
| TCGAGTTATC | AGGATCTCAG | GTTTGTGTCA | AATTTGTCAT | ATGTCTGTTT | CAGAATCTGG | 60 |
| CCTGCTCTGG | GGGATCCGTC | TTCCAGTTCT | CTCATCAGTG | CCTGGAAACA | AAATGCTGCC | 120 |
| TGTGCATTCT | GAATGGAATA | ACGCTGGCCT | TCGGGAATAT | ATGCTCTGTC | GGATGTGCCA | 180 |
| AAAACCAGGG | AATTCGTAAA | | | | | 200 |